(12) United States Patent
Marzouk et al.

(10) Patent No.: US 8,709,820 B2
(45) Date of Patent: Apr. 29, 2014

(54) CONCENTRATION MEASURING APPARATUS FOR HYDROGEN SULFIDE IN GAS FLOW, AND METHOD FOR DETERMINING SULFIDE ION

(75) Inventors: Sayed Marzouk, Al Ain (AE); Mohamed Al Marzouqi, Al Ain (AE)

(73) Assignees: Japan Cooperation Center, Petroleum, Tokyo (JP); United Arab Emirates University, Al Ain (AE)

( * ) Notice: Subject to any disclaimer, the term of this patent is extended or adjusted under 35 U.S.C. 154(b) by 401 days.

(21) Appl. No.: 13/036,535

(22) Filed: Feb. 28, 2011

(65) Prior Publication Data
US 2011/0217787 A1    Sep. 8, 2011

(30) Foreign Application Priority Data

Mar. 2, 2010    (JP) ................... 2010-045429

(51) Int. Cl.
*G01N 25/48*    (2006.01)
*G01N 25/42*    (2006.01)
(52) U.S. Cl.
USPC ............ 436/119; 422/51; 422/83; 422/88; 436/52; 436/121; 436/147; 436/177; 436/178; 436/181
(58) Field of Classification Search
USPC ............ 422/51, 83, 88; 436/52, 119, 121, 436/147.177–178, 181
See application file for complete search history.

(56) References Cited

U.S. PATENT DOCUMENTS

| | | | |
|---|---|---|---|
| 3,479,257 A | | 11/1969 | Shaver |
| 3,567,383 A | | 3/1971 | Langley et al. |
| 3,716,333 A | * | 2/1973 | Peuschel et al. ............... 436/79 |
| 3,716,337 A | * | 2/1973 | Jones ............................. 422/88 |
| 3,901,067 A | | 8/1975 | Boardman, Jr. et al. |
| 3,911,080 A | * | 10/1975 | Mehl et al. ................... 423/210 |
| 4,030,340 A | | 6/1977 | Chang |
| 4,042,328 A | * | 8/1977 | Seymour ........................ 436/52 |

(Continued)

FOREIGN PATENT DOCUMENTS

| | | |
|---|---|---|
| JP | 61-096446 | 5/1986 |
| JP | 2-088956 | 3/1990 |

(Continued)

OTHER PUBLICATIONS

Tarver, G. A. et al, Atmospheric Environment 1995, 29, 1291-1298.*

(Continued)

*Primary Examiner* — Arlen Soderquist
(74) *Attorney, Agent, or Firm* — Greenblum & Bernstein, P.L.C.

(57) ABSTRACT

A concentration measuring apparatus for hydrogen sulfide includes an absorbing liquid that can absorb gaseous hydrogen sulfide as sulfide ion; a hollow fiber membrane contactor that contacts a gas flow with a flow of the absorbing liquid through a membrane, so that the absorbing liquid absorbs gaseous hydrogen sulfide in the gas flow as sulfide ion; a pump for a first channel that feeds the absorbing liquid to the hollow fiber membrane contactor; an oxidizer that exothermically reacts with sulfide ion; a pump for a second channel that feeds the oxidizer to the absorbing liquid; a first thermometer that measures a temperature of the absorbing liquid before the sulfide ion that the absorbing liquid has absorbed exothermically reacts with the oxidizer; and a second thermometer that measures the temperature of the absorbing liquid after the sulfide ion that the absorbing liquid has absorbed exothermically reacts with the oxidizer.

7 Claims, 13 Drawing Sheets

(56) References Cited

U.S. PATENT DOCUMENTS

| | | | |
|---|---|---|---|
| 4,151,260 A * | 4/1979 | Woertz | 423/224 |
| 4,163,044 A * | 7/1979 | Woertz | 423/234 |
| 4,170,455 A * | 10/1979 | Henrie | 436/144 |
| 4,268,279 A * | 5/1981 | Shindo et al. | 95/46 |
| 4,407,963 A * | 10/1983 | Sorensen | 436/147 |
| 4,493,716 A * | 1/1985 | Swick | 96/12 |
| 4,548,708 A * | 10/1985 | Schwarzer et al. | 208/196 |
| 4,767,601 A * | 8/1988 | Kuerzinger et al. | 422/82.12 |
| 4,783,317 A * | 11/1988 | Kuerzinger et al. | 422/82.12 |
| 5,173,264 A * | 12/1992 | Zaromb et al. | 422/88 |
| 5,254,143 A * | 10/1993 | Anazawa et al. | 95/46 |
| 6,355,092 B1 * | 3/2002 | Jansen et al. | 95/45 |
| 2003/0134426 A1 * | 7/2003 | Jiang et al. | 436/121 |
| 2007/0286783 A1 * | 12/2007 | Carrette et al. | 423/228 |

FOREIGN PATENT DOCUMENTS

| | | | |
|---|---|---|---|
| JP | 2003-210936 | | 7/2003 |
| JP | 2005-16116 | | 8/2006 |
| JP | 2009-128017 | | 6/2009 |
| JP | 2009-128017 | * | 6/2013 |

OTHER PUBLICATIONS

Huang, H. et al, Electroanalysis 1997, 9, 585-591.*
Toda, K. et al, Analytical Chemistry 2001, 73, 5716-5724.*
Wang, D. et al, Separatin and Purification Technology 2002, 27, 33-40.*
Toda, K. et al, Environmental Science and Tencnology 2004, 38, 1529-1536.*
Couvert, A. et al, Chemical Engineering Science 2006, 61, 7240-7248.*
Couvert, A. et al, Chemosphere 2008, 70, 1510-1517.*
Boucif, N. et al, AIChE Jrournal 2008, 54, 122-131.*
Marzouk, S. A. M. et al, Microchemical Journal 2010, 95, 207-212.*
A.C. Aplin et al., "Sour Gas and Water Chemistry of the Bridport Sands Reservoir, Wytch Farm, UK", The Geochemistry of Reservoirs No. 86 The Geological Society, London, Special Publications, 1995, pp. 303-314.
John R. Dosher et al., "Sulfur Increase Seen Mostly in Heavy Fractions of Lower-quality Crudes", Chiyoda Receives TQM Award_ Chiyoda Corporation Oil & Gas, 1994, pp. 42-48.
Mike R. Carlson et al., "Obtaining PVT Data for Very Sour Retrograde Condensate Gas", SPE International Society of Petroleum Engineers, Inc., 1996, pp. 691-706.
Joaquim Font et al., "Determination of sulfide in the leather industry by capillary electrophoresis", Journal of Chromatography A vol. 740 1996, pp. 125-132.
Delmar R. Salomon et al., "Applications of capillary ion electrophoresis in the pulp and paper industry", Journal of Chromatography vol. 602_1992, pp. 219-225.
Nathan S. Lawrence et al., "Analytical strategies for the detection of sul?de: a review", TALANTA vol. 52 2000, pp. 771-784.
"A Comprehensive Guide to the Hazardous Properties of Chemical Substances", Pradyot Patnaik, Ph.D. Third Edition A John Wiley & Sons, Inc., 1999, pp. 407.
Wojciech Puacz et al., "Catalytic Determination of Sulfide in Blood*", Analyst vol. 120, 1995, pp. 939-941.
Wilson L. Orr et al., "Geochemistry of Sulfur in Petroleum Systems", Geochemistry of Sulfur in Fossil Fuels_ACS Symposium Series; American Chemical Society, Jun. 29, 1990, pp. 2-29.
Laura Ferrer et al., "Analytical Methodologies for Reliable Sul?de Determinations in Aqueous Matrices Exploiting Flow-Based Approaches", Trends in Analytical Chemistry, vol. 26, No. 5., 2007, pp. 413-422.
Von B. Meyer, "Suffer Energy, and Environment", Elsevier Scientific Publishing Company, 1977 (3 pages total; includes bibliographic page, abstract page, and English-language translation of abstract).
R.D. Kane et al., "Wet $H_2S$ Cracking of Carbon Steels and Weldments", NACE International, Houston, 1996 (8 pages total; includes cover page, bibliographic page, additional cover page, page iv, chapter cover page, pp. 285, 286, and 359).
Aaron J. Rollo et al., "Diode Array Process Analyzer—For Sulfur Recovery Applications", Instrumentation, Systems, and Automation Society. ISA 52nd Division Symposium, 2007, pp. 1-12.

* cited by examiner

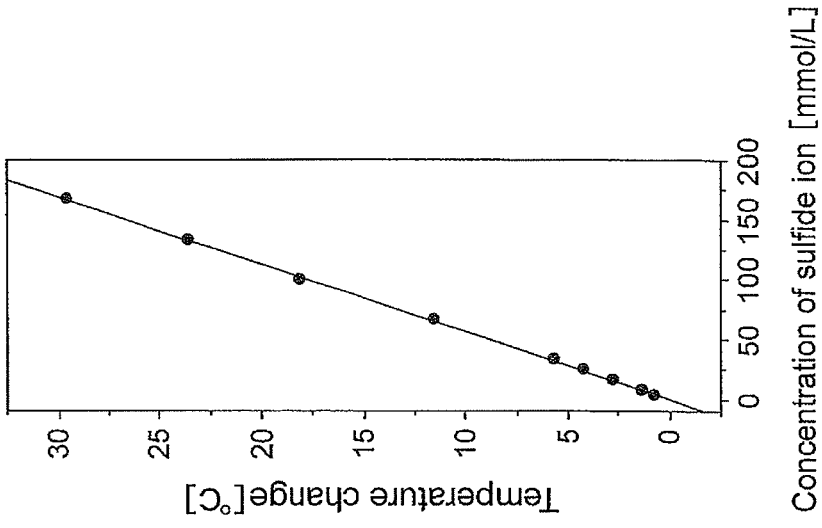
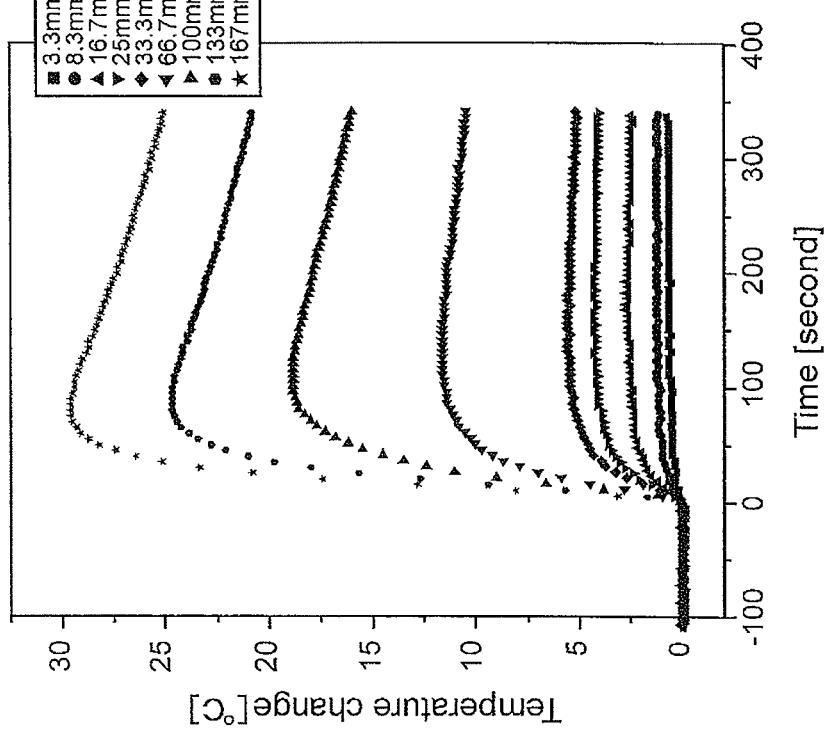
Fig. 1A
Fig. 1B

CONCENTRATION MEASURING APPARATUS FOR HYDROGEN SULFIDE IN GAS FLOW, AND METHOD FOR DETERMINING SULFIDE ION

BACKGROUND OF THE INVENTION

1. Field of the Invention

The present invention relates to a concentration measuring apparatus for hydrogen sulfide in a gas flow and a method for deter mining sulfide ion.

2. Related Background Art

Hydrogen sulfide ($H_2S$) is a poisonous and highly corrosive gas. Many working environments are accompanied by the risk of poisoning by $H_2S$. A human nose may sense $H_2S$ from a concentration of $H_2S$ as low as approximately 0.02 ppm, and the maximum sensitivity is usually approximately 5 ppm. Because the olfactory nerve begins to be paralyzed under the influence of a neurotoxin by $H_2S$ with a higher concentration (or exposure to $H_2S$ for a long time), the sensing ability of the gas is reduced (for example, see Literature 1 (P. Patnaik, "A ComprehensiveGuide to the Hazardous Properties of Chemical Substances", second ed., Wiley, New York, N.Y., 1999.) and Literature 2 (W. Puacz, W. Szahun, Analyst 120, (1995) 939.)).

Contribution of hydrogen sulfide to the total sulfur content in an environment (the air) is relatively limited. Emission of $H_2S$ to the environment (the air) is mainly attributed to industrial areas (particularly petrochemical industry) concentrated on a specific place (for example, see Literature 3 (W. L. Orr, J. S. "SinningheDamste, Geochemistry of sulfur in petroleum systems", in: W. L. Orr, C. M. White (Eds.), "Geochemistry of Sulfur in Fossil Fuels", ACS Symposium Series 429, American Chemical Society, Washington, D.C., 1990, pp. 2-9."), Literature 4 (A. C. Aplin, M. L. Coleman, "Sour gas and water chemistry of the Bridgeport Sands reservoir", Wytch Farm, UK, in: J. M. Cubitt, W. A. England (Eds.), "The Geochemistry of Reservoirs", The Geological Society, London, UK, 1995, pp. 303-314 Geol Soc. Special Publication 86.), and Literature 5 (R. D. Kane, R. J. Horvath, M. S. Cayard (Eds.), "Wet $H_2S$ cracking of carbon steels and weldments", NACE International, Houston, 1996.)). Hydrogen sulfide exists widely in a hydrocarbon storage layer under the ground under an anaerobic condition as a result of interaction of sulfate-reducing bacteria and exogenous sulfate (see the above Literatures 3 and 4, for example). Generally, the proportion of sulfur contained in crude oil is in the range of 0.3 to 0.8 wt %, and the proportion of hydrogen sulfide contained in natural gas is in the range of 0.01 to 0.4 wt %. While it has been reported that the concentration of hydrogen sulfide in the natural gas is 30 wt % at the maximum (for example, see Literature 6 (Dosher, J. R and Carney J. T., "Sulfur increase seen mostly in heavy fractions of lower-quality crudes" Oil & Gas J., 92, 42-48 (1994).), it is recognized that the proportion of sulfur contained in the crude oil and that in the natural gas have been increased steadily for the past decades, and further increase in the concentration of hydrogen sulfide is expected (for example, see Literature 7 (M. R. Carlson, W. B. Cawston, "Obtaining PVT data for very sour retrograde condensate gas and volatile oil reservoirs: A multi-disciplinary approach", SPE Gas Technology Conference, Calgary, Canada, April-May 1996, SPE 35653.)).

$H_2S$ is emitted as a by-product of biological action in recovery and processing of waste water. Although $H_2S$ considerably dissolves in water, most of bad smell problems caused by the waste disposal process are attributed to temporary emission of $H_2S$. In addition, sulfides are emitted to an aqueous environment through mobilization of sulfur containing inorganic substances by microorganisms (for example, see Literature 8 (B. Meyer, "Sulfur Energy and the Environment", Elsevier, 1977.)). Leather article industry (for example, see Literature 9 (J. Font, J. Gutierrez, J. Lalueza, X. Perez, J. Chromatogr. A 740 (1996) 125.) and pulp and paper industry (for example, see Literature 10 (D. R. Saloman, J. Romano, J. Chromatogr. 602 (1992) 219.)) also greatly contribute to emission of $H_2S$ or $S^{2-}$ to an ecological system.

Because sulfide anions have high reactivity, development of many detecting methods ranging from more classic methods to span spectroscopic, chromatographic, electrochemical methods, and their combinations thereof have been possible. Reviews (surveys) including some of these methods have been reported (for example, see Literature 11 (N. S. Lawrence, J. Davis, R. G. Compton, Talanta 52 (2000) 771-784.) and Literature 12 (L. Ferrer, M. Miro, J. M. Estela, V. Cerda, Trends in Analytical Chemistry, 26 (2007) 413-422.)). However, most of the methods developed so far aim at measurement of sulfide anions in a solution, and the methods designed in order to measure $H_2S$ in a gas flow were few. As the methods designed in order to measure $H_2S$ in a gas flow, solid state gas sensors and gas analyzers based on ultraviolet absorption or a lead acetate tape method are known. As a detector (solid state gas sensor) using a semiconductor, those disclosed in the following Patent Literature 1 (U.S. Pat. No. 3,479,257), Patent Literature 2 (U.S. Pat. No. 3,901,067), Patent Literature 3 (U.S. Pat. No. 4,030,340) and Patent Literature 4 (U.S. Pat. No. 3,567,383) are known, for example. As an $H_2S$ analyzer based on ultraviolet absorption measurement in a flow cell (gas analyzer based on ultraviolet absorption), that disclosed in the following Non Patent Literature 1 (A. J. Rollo, "Diode ArrayProcess Analyzer—for Sulfur Recovery Applications", Instrumentation, Systems, and Automation Society, ISA 52nd Analysis Division Symposium, 2007) is known, for example.

The detector (solid state gas sensor) using a semiconductor utilizes a fact that a specific substance adsorbed by the semiconductor influences conductivity of a thin portion (segment) of a thin film in the vicinity of the surface of the semiconductor. These apparatuses are usually formed of a metal oxide semiconductor provided on an inactive substrate. For giving an influence to conductivity, a small amount of a dopant having a valence higher or lower than that of a metal oxide, namely, impurities may be added to the metal oxide. Further, in order to accelerate a reaction in a surrounding gas and to assist detection, a catalyst may be added to the surface of the semiconductor. These various apparatuses are disclosed in Patent Literatures 1 to 4 above, for example. These apparatuses and other apparatuses are subjected to one or more restrictions. For example, many of such apparatuses cannot provide sufficient life span. Other apparatuses depend on a catalyst for decomposing the gas to be detected. However, because the catalyst tends to be influenced by a catalyst poison, the life span of the apparatus is limited. Other apparatuses are greatly affected by moisture (humidity) in the gas. For that reason, it is difficult to sufficiently enhance reliability of the apparatus.

The lead acetate tape method for detecting hydrogen sulfide ($H_2S$) and total sulfur in a gaseous flow is based on an established principle that $H_2S$ reacts specifically with lead acetate to produce a brown lead sulfide pigment. The concentration of $H_2S$ is in direct proportion to a changing speed of coloring of a lead acetate tape. This principle serves as a basic principle of many ASTM (American Society for Testing and Materials) methods. This analyzer moves a processed paper tape by one partition at one time. According to the concentration of a sample, the color of the tape begins to be darken at a rate proportional to the concentration of $H_2S$ in the flow of the sample. This analyzer exposes a new partition of the tape to the sample in a sample chamber for every specific time (for example, every three minutes). Although this tape analyzer is reliable and is thought as a simple method, the tape analyzer can be used only for semi-continuous measurement because the reaction with a slow reaction rate is utilized.

Although the $H_2S$ analyzer based on ultraviolet absorption measurement in a flow cell can continuously measure $H_2S$ in a gas flow, the $H_2S$ analyzer cannot be available without considerably high cost, because it includes expensive components such as a xenon pulse light source and a diode array detector (see Non Patent Literature 1 above).

The present invention has been made in consideration of such problems; an object of the present invention is to provide a concentration measuring apparatus for hydrogen sulfide that can continuously measure hydrogen sulfide in a gas flow, and is inexpensive and reliable; and another object is to provide a method for determining sulfide ion in a liquid that can be used for such a concentration measuring apparatus for hydrogen sulfide.

SUMMARY OF THE INVENTION

The present invention discloses a novel method for determining sulfide ion in a liquid. This determination method is applied to an inexpensive and reliable concentration measuring apparatus for hydrogen sulfide that can continuously measure the concentration of $H_2S$ in a gas flow. The measuring apparatus is based on a commercially available hollow fiber membrane contactor that acts as a diffusion scrubber for continuous sampling of a gas, and a new calorimetric detection method with respect to determination of hydrogen sulfide. An alkali carrier solution absorbs hydrogen sulfide from the gas flow in the membrane contactor, and then merges into other solution to react with the other solution. The other solution is hydrogen peroxide in one Example, and hypochlorite in other Example. The solution oxidizes the sulfide anions to sulfate by a strong exothermic reaction. Increase of the temperature of the solution by the exothermic reaction is measured, and an analysis signal proportional to hydrogen sulfide in the gas flow is given. Advantages of the present invention include the following (1) to (8).

(1) The method for determining sulfide ion in a liquid according to the present invention is inexpensive, simple, and direct, and has proper selectivity. (2) The measuring apparatus according to the present invention can continuously measure the concentration of $H_2S$ in a wide operating range ranging from a ppm level to a percent level. (3) The measuring apparatus according to the present invention can measure $H_2S$ in the gas with higher selectivity than in the case of measurement of sulfide in a liquid. (4) In the measuring apparatus according to the present invention, a sensitivity range can be easily adjusted according to a degree of preconcentration of sulfide ion in a membrane module as the membrane contactor (specifically, a degree of preconcentration of $H_2S$ in the gas flow as sulfide ion in an absorbing liquid in a membrane module). (5) Because the measuring apparatus according to the present invention employs temperature difference measurement, the base line at the time of measuring increase in the temperature is stabilized. (6) In the measuring apparatus according to the present invention, precise control of the temperature of a reagent is unnecessary. (7) The measuring apparatus according to the present invention has a simple structure. (8) Manufacturing cost and operating cost of the measuring apparatus according to the present invention are low.

In order to solve the above-mentioned problems associated with present art, a measuring apparatus according to the present invention is a measuring apparatus that measures a concentration of gaseous hydrogen sulfide in a gas flow, the measuring apparatus comprising: an absorbing liquid that can absorb gaseous hydrogen sulfide as sulfide ion; a membrane contactor that contacts the gas flow with a flow of the absorbing liquid through a membrane, so that the absorbing liquid absorbs at least part of gaseous hydrogen sulfide in the gas flow as sulfide ion; an absorbing liquid feeder that feeds the absorbing liquid to the membrane contactor; an oxidizer that exothermically reacts with sulfide ion; an oxidizer feeder that feeds the oxidizer to the absorbing liquid; a first thermometer that measures a temperature of the absorbing liquid before the sulfide ion that the absorbing liquid has absorbed exothermically reacts with the oxidizer; and a second thermometer that measures the temperature of the absorbing liquid after the sulfide ion that the absorbing liquid has absorbed exothermically reacts with the oxidizer.

According to the measuring apparatus of the present invention, intensity of the exothermic reaction of the sulfide ion derived from the gaseous hydrogen sulfide in the gas flow to be measured, which the absorbing liquid has absorbed, with the oxidizer can be measured by the first thermometer and the second thermometer. Absorption of the gaseous hydrogen sulfide in the gas flow by the absorbing liquid (namely, movement of the gaseous hydrogen sulfide into the absorbing liquid from the gas flow and an absorption reaction of the gaseous hydrogen sulfide by the absorbing liquid) occurs immediately when the absorbing liquid and the gas flow contact each other through the membrane of the membrane contactor, and the exothermic reaction of the sulfide ion with the oxidizer occurs immediately when these are mixed. Thus, the measuring apparatus according to the present invention can continuously measure the gaseous hydrogen sulfide in the gas flow because the measuring apparatus utilizes a mass transfer phenomenon at a fast transfer rate and a reaction at a fast reaction rate.

In the absorption reaction of the gaseous hydrogen sulfide by the absorbing liquid and the exothermic reaction of the sulfide ion with the oxidizer, a catalyst is unnecessary. Moreover, because $H_2S$ in the gas flow is selectively absorbed by the absorbing liquid using the membrane of the membrane contactor even if moisture is contained in the gas flow, almost no influence is given to a measured value by the moisture in the gas flow. Moreover, in the measuring apparatus according to the present invention, a component that limits the life span of the apparatus as that in the conventional measuring apparatus is unnecessary. For these reasons, reliability of the measuring apparatus according to the present invention is enhanced. Further, to exothermically react the sulfide ion with the oxidizer and to measure intensity of this exothermic reaction, a complicated component and an expensive component are unnecessary. For that reason, in the measuring apparatus according to the present invention, the configuration thereof is simple and the price thereof is inexpensive.

Further, in the measuring apparatus according to the present invention, the absorbing liquid is preferably an alkaline solution. Thereby, the absorbing liquid can efficiently absorb the gaseous hydrogen sulfide in the gas flow as sulfide ion.

Further, in the measuring apparatus according to the present invention, the oxidizer can be hydrogen peroxide or hypochlorite. Thereby, efficiency of the exothermic reaction of the absorbing liquid with the oxidizer can be increased.

Further, the measuring apparatus according to the present invention can further include a first container that stores the absorbing liquid and a second container that stores the oxidizer.

In the measuring apparatus according to the present invention, the oxidizer feeder can feed the oxidizer to the absorbing liquid after the absorbing liquid absorbs at least part of the gaseous hydrogen sulfide. Thereby, a material that may deteriorate the membrane contactor can also be used as the oxidizer, and therefore, the range of selection of the materials used as the oxidizer and those as the membrane contactor is widened. In addition, even if an absorbing liquid whose efficiency of absorption of the gaseous hydrogen sulfide is reduced when the temperature is increased is used, the gaseous hydrogen sulfide can be absorbed by the absorbing liquid before the sulfide ion reacts with the oxidizer to increase the temperature of the absorbing liquid; therefore, reduction in efficiency of absorption of the gaseous hydrogen sulfide by the absorbing liquid, which is attributed to increase in the temperature, can be suppressed.

Further, in the measuring apparatus according to the present invention, the oxidizer feeder can feed the oxidizer to the absorbing liquid in a region in the vicinity of a liquid discharging end of the membrane contactor.

Moreover, in the measuring apparatus according to the present invention, the oxidizer feeder can feed the oxidizer to the absorbing liquid before the absorbing liquid absorbs at least part of the gaseous hydrogen sulfide.

Further, in the measuring apparatus according to the present invention, the oxidizer feeder can feed the oxidizer to the absorbing liquid in a region in the vicinity of a liquid introducing end of the membrane contactor.

Moreover, the measuring apparatus according to the present invention can further include a third container that stores a liquid mixture of the absorbing liquid and the oxidizer. Thereby, the storage container of the absorbing liquid and the storage container of the oxidizer can be shared, and the feeder of the absorbing liquid and the feeder of the oxidizer can be shared; therefore, the structure of the measuring apparatus is simplified, and a more inexpensive measuring apparatus can be provided.

Moreover, in order to solve the above-mentioned problems, a determination method according to the present invention is a method for determining sulfide ion in a liquid, the method comprising: an exothermic reaction step of exothermically reacting sulfide ion in a liquid with an oxidizer; and a calculating step of calculating a determination value of the sulfide ion based on a difference between a temperature of the liquid before the exothermic reaction step and a temperature of the liquid after the exothermic reaction step.

According to the determination method of the present invention, intensity of the exothermic reaction of sulfide ion in a liquid to be determined with the oxidizer can be calculated from a difference between the temperature of the liquid before the exothermic reaction is made and that after the exothermic reaction is made. The exothermic reaction of the sulfide ion with the oxidizer is made immediately when these are mixed. Thus, because the determination method according to the present invention uses a reaction at a fast reaction rate, the determination method can continuously determine the sulfide ion in the flow of the liquid even if the liquid flows.

Further, in the exothermic reaction of the sulfide ion with the oxidizer, a catalyst is unnecessary. For that reason, reliability of determination is enhanced. Further, to exothermically react the sulfide ion with the oxidizer and to measure intensity of this exothermic reaction, a complicated component and an expensive component are unnecessary. Thereby, the determination method according to the present invention can be implemented as an inexpensive apparatus with a simple configuration. For that reason, the determination method according to the present invention can be used for the above concentration measuring apparatus for hydrogen sulfide.

Further, in the determination method according to the present invention, the oxidizer is preferably hydrogen peroxide or hypochlorite. Thereby, efficiency of the exothermic reaction of the liquid with the oxidizer can be increased.

According to the present invention, an inexpensive and reliable concentration measuring apparatus for hydrogen sulfide that can continuously measure hydrogen sulfide in a gas flow is provided, and a method for determining sulfide ion in a liquid that can be used for such a concentration measuring apparatus for hydrogen sulfide is provided.

BRIEF DESCRIPTION OF THE DRAWINGS

FIG. 1A is a diagram showing the calorimetric response to sulfide ion in an $H_2O_2$ aqueous solution with a concentration of 1.5 mol/L in a calorimeter made of polyethylene with a volume of 15 mL.

FIG. 1B is a diagram showing the calorimetric response to sulfide ion in an $H_2O_2$ aqueous solution with a concentration of 1.5 mol/L in a calorimeter made of polyethylene with a volume of 15 mL.

DESCRIPTION OF THE PREFERRED EMBODIMENTS

Figure 2B:
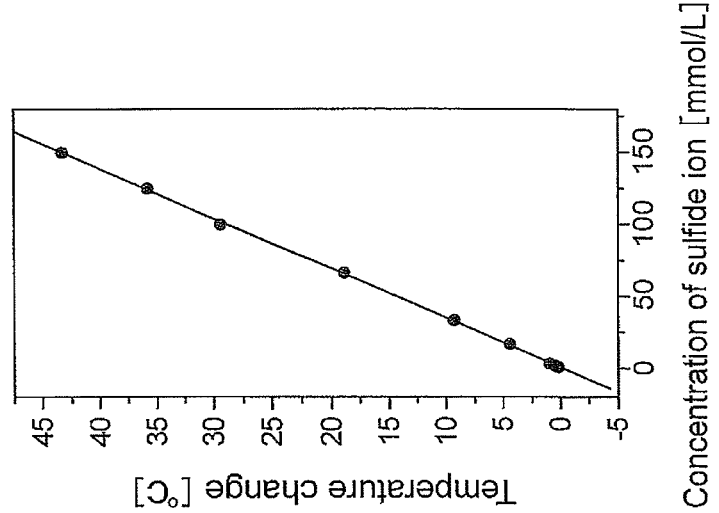
FIG. 2B is a diagram showing response of calorimetry to sulfide ion in a 1.5 mol/L $H_2O_2$ aqueous solution in a calorimeter made of polystyrene foam with a volume of 150 mL.

Hereinafter, a concentration measuring apparatus for hydrogen sulfide and a method for determining sulfide ion according to an embodiment will be described in detail with reference to the accompanying drawings. In each drawing, if possible, identical reference numerals are used for identical elements. Each size ratio within a component and that between components in the drawings are arbitrary because of clearness of the drawings.

The method for determining sulfide ion according to the present embodiment is based on new application of heat emitted from an oxidation reaction of sulfide ion by hydrogen peroxide in an alkaline aqueous solution, as shown in an expression 1.

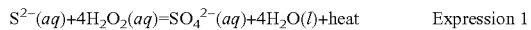

$$S^{2-}(aq)+4H_2O_2(aq)=SO_4^{2-}(aq)+4H_2O(l)+\text{heat} \qquad \text{Expression 1}$$

The following three important advantages are recognized in this exothermic reaction, and contribute to the concentration measuring apparatus for hydrogen sulfide and the method for determining sulfide ion according to the present embodiment.

(1) Unlike an ordinary oxidation reaction of sulfide, a product of this exothermic reaction is a soluble sulfate, not an insoluble element (simple substance) sulfur.

(2) The reaction is more exothermic in alkaline media which are extremely suitable for fixing sulfide ions in liquids as well as for efficient $H_2S$ stripping from gas streams.

(3) Because the heat of reaction of this exothermic reaction is large, produced temperature change can be used as an analysis signal suitable for determining sulfide ion.

Interestingly, the above advantages are not obtained in a reaction in a weak acidic medium shown in an expression 2.

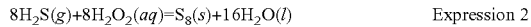

$$8H_2S(g)+8H_2O_2(aq)=S_8(s)+16H_2O(l) \qquad \text{Expression 2}$$

Figure 2A:
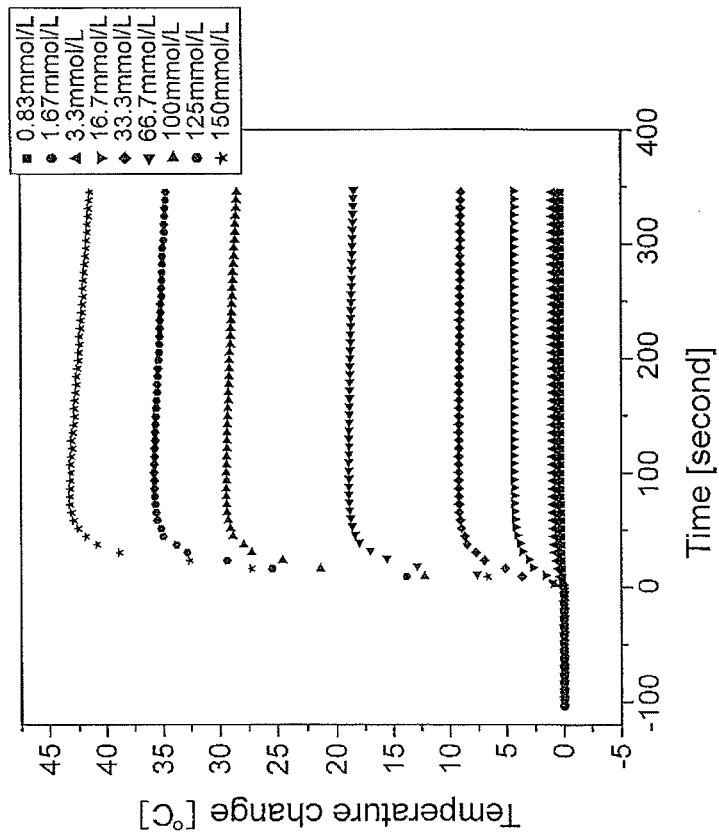
FIG. 2A is a diagram showing the calorimetric response to sulfide ion in a 1.5 mol/L $H_2O_2$ aqueous solution in a calorimeter made of polystyrene foam with a volume of 150 mL.

FIGS. 1A and 1B are diagrams showing the calorimetric response to sulfide ion in an $H_2O_2$ aqueous solution with a concentration of 1.5 mol/L in a calorimeter made of polyethylene with a volume of 15 mL. FIG. 1A is a diagram showing a temperature-time curve, in which time zero means the instant when sulfide ion is added, and plotting is made for each concentration of the added sulfide ion. FIG. 1B is a diagram showing a calibration curve corresponding to FIG. 1A, in which plotting is made based on the highest temperature in the curve for each mol concentration of sulfide ion in FIG. 1A. FIGS. 2A and 2B are diagrams showing the calorimetric response to sulfide ion in a 1.5 mol/L $H_2O_2$ aqueous solution in a calorimeter made of a foamed plastic with a volume of 150 mL. FIG. 2A is a diagram showing a temperature-time curve, in which time zero means the instant when sulfide ion is added, and plotting is made for each concentration of the added sulfide ion. FIG. 2B is a diagram showing a calibration curve corresponding to FIG. 2A, in which plotting is made based on the highest temperature in the curve for each concentration of sulfide ion in FIG. 2A.

Analysis practicability of the calorimetric (thermometric) method disclosed for determining sulfide ion in the aqueous solution is clear in FIGS. 1A. 1B, 2A and 2B showing the result obtained by the calorimeter made of polyethylene and the result obtained by the calorimeter made of a foamed plastic, respectively. The observed temperature change ($\Delta T$) is given by an expression 3.

$$\Delta T = K \times C \times \Delta H \qquad \text{Expression 3}$$

Here, K is a constant related to the heat capacity of the entire system, C is a sulfide ion concentration (in the case where an oxidizer is given excessively), and $\Delta H$ is the heat of reaction.

Because the measured analysis signal (namely, $\Delta T$) is in direct proportion to the reaction heat ($\Delta H$), some possible oxidizers were tested and it was proved that a hypochlorite solution reacts with sulfide as hydrogen peroxide does; however, the value of $\Delta H$ in the case where the hypochlorite solution was used as the oxidizer was approximately 60% of that of $\Delta H$ in the case where hydrogen peroxide was used as the oxidizer.

Figure 3:
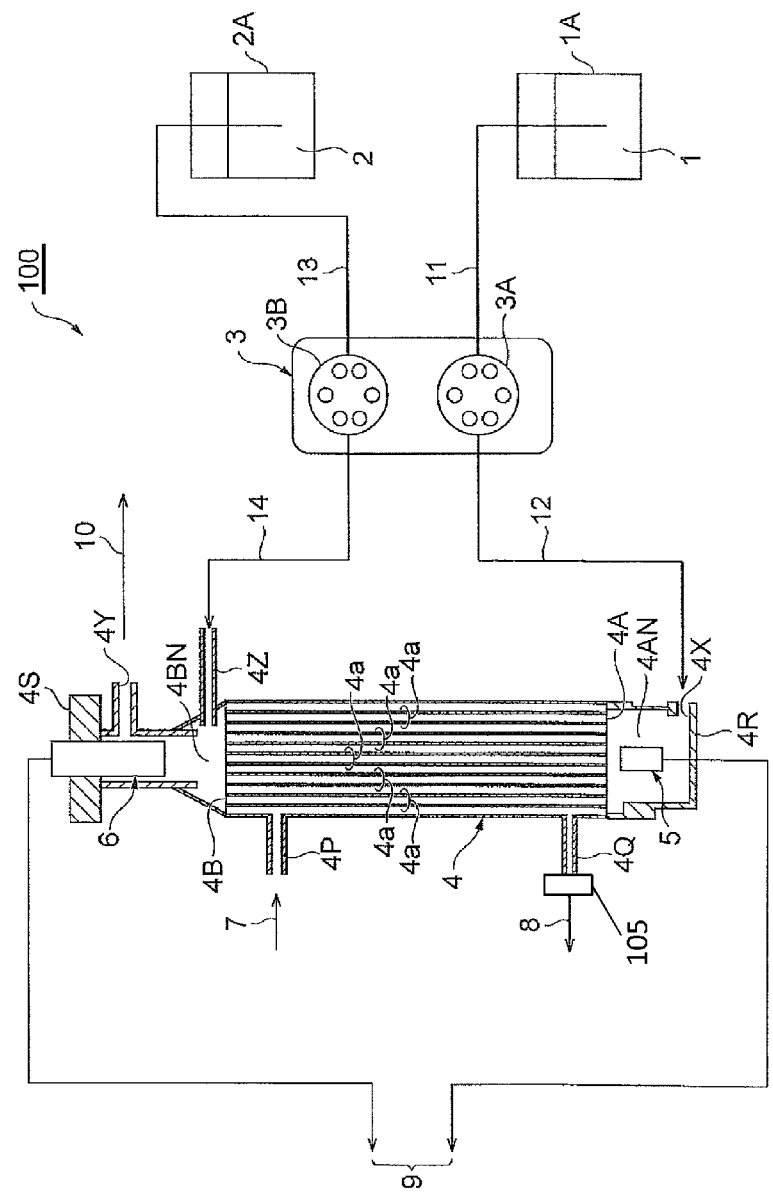
FIG. 3 is a schematic view showing a configuration of a concentration measuring apparatus for hydrogen sulfide according to an embodiment.
Figure 4A:
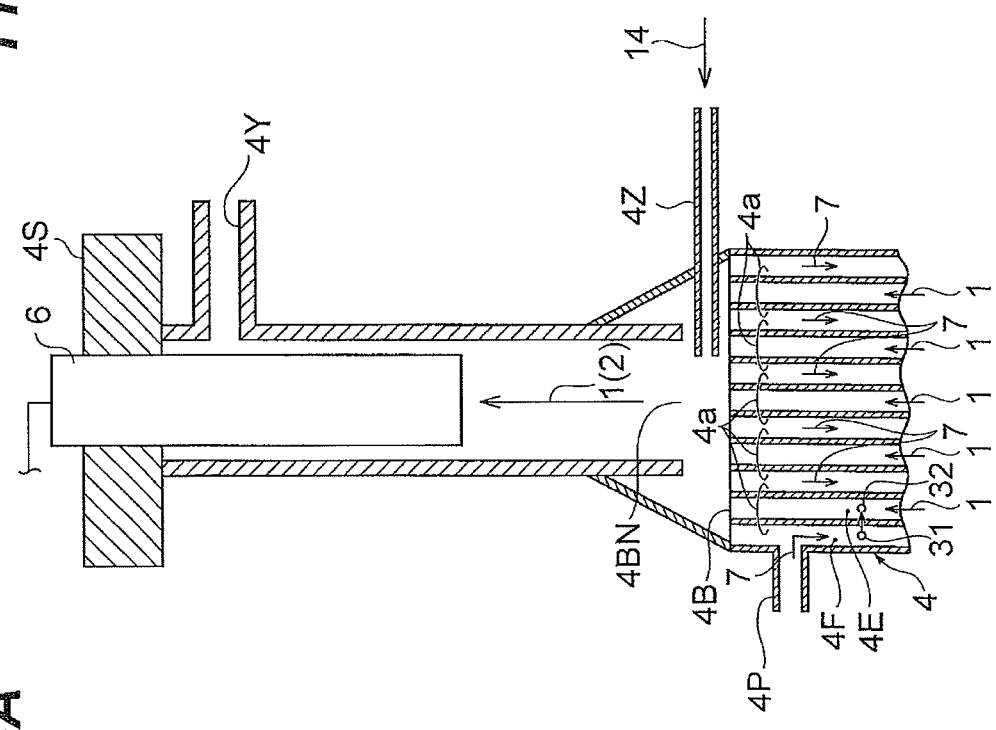
FIG. 4A is a schematic view showing a configuration in a region in the vicinity of a liquid discharging end of the concentration measuring apparatus for hydrogen sulfide.
Figure 4B:
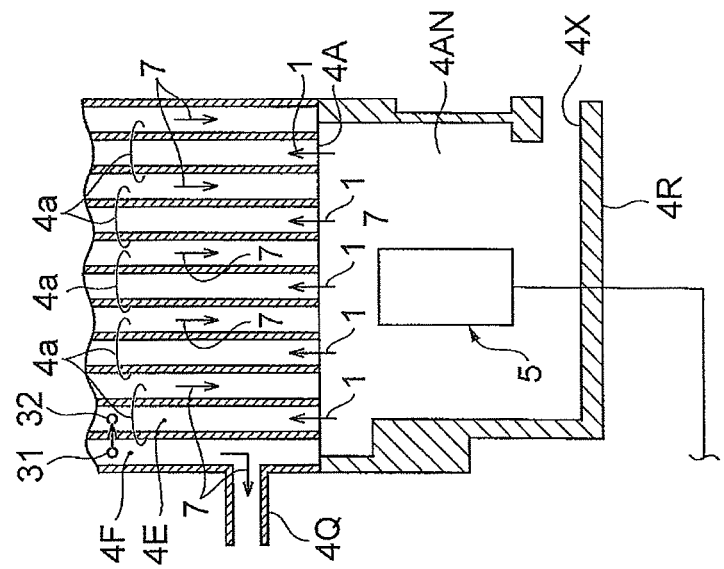
FIG. 4B is a schematic view showing a configuration in a region in the vicinity of a liquid introducing end of the concentration measuring apparatus for hydrogen sulfide.

FIG. 3 is a schematic view showing a configuration of a concentration measuring apparatus for hydrogen sulfide according to the present embodiment. FIG. 4A is a schematic view showing a configuration in a region in the vicinity of a liquid discharging end of the concentration measuring apparatus for hydrogen sulfide. FIG. 4B is a schematic view showing a configuration in a region in the vicinity of a liquid introducing end of the concentration measuring apparatus for hydrogen sulfide. As shown in FIG. 3, the concentration measuring apparatus for hydrogen sulfide 100 according to the present embodiment includes an absorbing liquid 1, a first container 1A that stores the absorbing liquid 1, an oxidizer 2 that exothermically reacts with sulfide ion, a second container 2A that stores the oxidizer 2, a pump unit 3 of two channels as an absorbing liquid feeder and an oxidizer feeder, a hollow fiber membrane contactor 4 as a membrane contactor, a first thermometer 5, and a second thermometer 6.

The method for determining sulfide ion according to the present embodiment is used for the concentration measuring apparatus for hydrogen sulfide 100 shown in FIG. 3.

As shown in FIGS. 3, 4A, and 4B, the hollow fiber membrane contactor 4 has one or a plurality of hollow fibers 4a. The hollow fiber membrane contactor 4 has function to contact gaseous hydrogen sulfide in the gas that exists on a shell side 4F (the outer side of each hollow fiber 4a) of the hollow fiber membrane contactor 4 to a tube side 4E (the inside of each hollow fiber 4a, namely, a hollow portion of each hollow fiber 4a) of the hollow fiber membrane contactor 4 containing the absorbing liquid 1.

An inlet side flow cell 4R that defines a region 4AN in the vicinity of a liquid introducing end 4A is provided in the region 4AN in the vicinity of the liquid introducing end 4A, which is the inlet on the tube side 4E of the hollow fiber membrane contactor 4. An introducing opening 4X that communicates with the liquid introducing end 4A is formed in the inlet side flow cell 4R. An outlet side flow cell 4S that defines a region 4BN in the vicinity of the liquid discharging end 4B is provided in the region 4BN in the vicinity of the liquid discharging end 4B, which is an outlet on the tube side 4E of the hollow fiber membrane contactor 4. A discharging opening 4Y that communicates with the liquid discharging end 4B is formed in the outlet side flow cell 4S.

The pump unit 3 is a two-channel pump in the present embodiment. Specifically, the pump unit 3 has a pump 3A for a first channel and a pump 3B for a second channel. The pump 3A for the first channel is connected with the first container 1A by a piping 11, and is connected to the introducing opening 4X of the hollow fiber membrane contactor 4 by a piping 12. The pump 3A for the first channel functions as an absorbing liquid feeder. Specifically, the pump 3A for the first channel feeds the absorbing liquid 1 to the region 4AN in the vicinity of the liquid introducing end 4A through the piping 11, the piping 12, and the introducing opening 4X, thereby to continuously feed the absorbing liquid 1 from the liquid introducing end 4A to the tube side 4E of the hollow fiber membrane contactor 4. The first thermometer 5 is provided in the region 4AN in the vicinity of the hollow fiber membrane contactor 4, and continuously measures the temperature of the absorbing liquid 1 fed to the hollow fiber membrane contactor 4.

A gas flow 7 is a flow of a gas containing gaseous hydrogen sulfide. The gas flow 7 passes through a piping 4P formed with a plastic tube or the like and provided in the vicinity of the inlet on the shell side 4F of the hollow fiber membrane contactor 4, and enters the shell side 4F of the hollow fiber membrane contactor 4. The gas flow 7 that enters the shell side 4F of the hollow fiber membrane contactor 4 contacts the absorbing liquid 1 fed to the tube side 4E of the hollow fiber membrane contactor 4 through each hollow fiber 4a of the hollow fiber membrane contactor 4. Thereby, the absorbing liquid 1 absorbs at least part of gaseous hydrogen sulfide 31 in the gas flow 7 as sulfide ion 32. Subsequently, the gas flow 7 is discharged to the outside as an exhaust gas 8 through a piping 4Q, such as a reduced pressure piping provided in the vicinity of the outlet on the shell side 4F of the hollow fiber membrane contactor 4. Preferably, the exhaust gas 8 passes through an eliminating apparatus such as an alkali trap 105, and is discharged to the outside.

The absorbing liquid 1 that has absorbed at least part of the gaseous hydrogen sulfide in the gas flow 7 as the sulfide ion comes out from the liquid discharging end 4B of the hollow fiber membrane contactor 4, and is discharged to the outside as a waste liquid 10 from the discharging opening 4Y through the region 4BN in the vicinity of the liquid discharging end 4B.

The pump 3B for the second channel is connected with the second container 2A by a piping 13, and is connected with an introducing opening 4Z by a piping 14, the introducing opening 4Z communicating with the liquid discharging end 4B of the hollow fiber membrane contactor 4. The pump 3B for the second channel functions as an oxidizer feeder. Specifically, the pump 3B for the second channel continuously feeds the oxidizer 2 to the region 4BN in the vicinity of the liquid discharging end 4B through the piping 13, the piping 14, and the introducing opening 4Z, thereby to feed the oxidizer 2 to the absorbing liquid 1. Thereby, the sulfide ion in the absorbing liquid 1 is exothermically reacted with the oxidizer 2 (the exothermic reaction step).

As the pump 3A for the first channel and the pump 3B for the second channel, pumps such as a peristaltic pump, a rotary pump, or a reciprocal pump can be used, for example. Use of a peristaltic pump as the pump 3A for the first channel or the pump 3B for the second channel is preferable in a point that the pump is inexpensive and in a point that pulsation is little.

In the present embodiment, the absorbing liquid feeder and the oxidizer feeder are integrated. Specifically, the pump 3A for the first channel and the pump 3B for the second channel are integrated as the pump unit 3, while the absorbing liquid feeder and the oxidizer feeder may be separate bodies. For example, the concentration measuring apparatus for hydrogen sulfide 100 may have two separate pumps instead of the pump unit 3. In this case, the concentration measuring apparatus for hydrogen sulfide 100 has a first pump as the absorbing liquid feeder and a second pump as the oxidizer feeder instead of the pump unit 3.

The oxidizer 2 is a material that exothermically reacts with sulfide ion. Specifically, hydrogen peroxide, hypochlorite, permanganate, or peroxydisulfuric acid salt can be used as the oxidizer 2.

In the region 4BN in the vicinity of the liquid discharging end 4B, the exothermic reaction as shown in the above expression 1 is made by mixing the absorbing liquid 1 with the oxidizer 2. The temperature of the absorbing liquid 1 after this exothermic reaction is continuously measured by the second thermometer 6 provided in the region 4BN in the vicinity of the liquid discharging end 4B. Then, based on a thermometry value 9 by the first thermometer 5 and that by the second thermometer 6, a temperature difference $\Delta T$ between the temperature of the absorbing liquid 1 before the exothermic reaction step and the temperature of the absorbing liquid 1 after the exothermic reaction step is determined. Then, based on this temperature difference $\Delta T$, the determination value of the sulfide ion 32 in the absorbing liquid 1 is calculated (the calculating step). This temperature difference $\Delta T$ serves as a basis of a new and reliable basic principle for the method for determining sulfide ion. Because the determination value of the sulfide ion 32 in the absorbing liquid 1 is calculated on the basis of the temperature difference between the temperature of the absorbing liquid 1 measured by the second thermometer 6 and that measured by the first thermometer 5, not the temperature of the absorbing liquid 1 measured by the second thermometer 6, an error of the calculated determination value of the sulfide ion 32 can be suppressed even if the temperature of the absorbing liquid 1 fluctuates due to a factor other than the exothermic reaction of the sulfide ion 32 with the oxidizer 2. Then, the concentration of the gaseous hydrogen sulfide 31 in the gas flow 7 is calculated from the thus-calculated determination value of the sulfide ion 32 in the absorbing liquid 1.

Preferably, the traveling direction of the of the gas flow 7 on the shell side 4F of the hollow fiber membrane contactor 4 is in the direction opposite to the flow direction of the absorbing liquid 1 on the tube side 4E of the hollow fiber membrane contactor 4. This is because comparing with the case where the traveling direction of the gas flow 7 on the shell side 4F of the hollow fiber membrane contactor 4 is in the same direction as the flow direction of the absorbing liquid 1 on the tube side 4E of the hollow fiber membrane contactor 4, a difference between the $H_2S$ concentration in the gas flow 7 and the concentration of the sulfide ion 32 in the absorbing liquid 1 is increased in the vicinity of the liquid discharging end 4B of the hollow fiber membrane contactor 4, and therefore, absorption efficiency of the sulfide ion 32 by the absorbing liquid 1 is improved.

The hollow fiber membrane contactor 4 is a commercially available compact module based on a microporous polypropylene (PP) hollow fiber (for example, U.S.A. Membrana G543), for example. The polypropylene hollow fiber is more suitable than other possible silicone rubber (SR) hollow fibers. This is because that resistance against the alkaline solution is better than that of non-porous silicone rubber hollow fibers, and it is expected that the gas flow flux that passes through the microporous hollow fiber is higher.

The absorbing liquid 1 is used as a first carrier liquid, and is preferably an alkaline solution from the viewpoint of increasing absorption efficiency of $H_2S$. When the absorption efficiency of $H_2S$ by the absorbing liquid 1 is increased, preconcentration efficiency in the hollow fiber membrane contactor 4 is increased, and eventually sensitivity of measurement of the $H_2S$ concentration by the concentration measuring apparatus for hydrogen sulfide 100 is increased. As the absorbing liquid 1, a sodium hydroxide aqueous solution, a potassium carbonate aqueous solution, or a potassium hydroxide solution can be used, for example. In the case where an alkaline solution is used as the absorbing liquid 1, $H_2S$ in the gas flow 7 is absorbed by the absorbing liquid 1 by physical absorption to water in the absorbing liquid 1 (dissolution to $H_2O$) and chemical absorption to an alkali in the absorbing liquid 1 (chemical reaction of $H_2S$ and the alkali, for example, a chemical reaction represented by a reaction formula, $H_2S+2NaOH \rightarrow S^{2-}+2Na^{+}+2H_2O$).

In the case where a combination of the absorbing liquid 1 and the oxidizer 2 that becomes unstable when the absorbing liquid 1 is mixed with the oxidizer 2 is selected as the combination of the absorbing liquid 1 and the oxidizer 2, it is preferable that the absorbing liquid 1 and the oxidizer 2 be stored in different containers (the first container 1A and the second container 2A), the absorbing liquid 1 be fed to the liquid introducing end 4A of the hollow fiber membrane contactor 4, and the oxidizer 2 be fed to the liquid discharging end 4B of the hollow fiber membrane contactor 4 as the present embodiment, rather than that the absorbing liquid 1 is mixed with the oxidizer 2 in advance and the liquid mixture is fed to the hollow fiber membrane contactor 4. In this case, the exothermic reaction of the sulfide ion with the oxidizer 2 is mainly made in the region 4BN in the vicinity of the liquid discharging end 4B.

The oxidizer 2 may be fed to the absorbing liquid 1 before the absorbing liquid 1 absorbs the at least part of the gaseous hydrogen sulfide as the sulfide ion. This can be implemented, for example, by providing the piping 14 between the pump 3B for the second channel as the oxidizer feeder and the introducing opening 4X, and feeding the oxidizer 2 to the region 4AN in the vicinity of the liquid introducing end 4A by the pump 3B for the second channel through the piping 13, the piping 14, and the introducing opening 4X. Thereby, the absorbing liquid 1 whose temperature is increased by the exothermic reaction of the sulfide ion 32 with the oxidizer 2 absorbs the gaseous hydrogen sulfide 31 in the gas flow 7.

However, as shown in FIG. 3, in the case where the oxidizer 2 is fed to the absorbing liquid 1 after the absorbing liquid 1 absorbs the at least part of the gaseous hydrogen sulfide as the sulfide ion, there exists an advantage that a range of selection of materials used as the oxidizer 2 and the hollow fiber membrane contactor 4 (particularly hollow fiber 4a) is widened. This is because a material that may deteriorate the hollow fiber membrane contactor 4 and particularly the hollow fiber 4a of the hollow fiber membrane contactor 4 can also be selected as the oxidizer 2. Thereby, for example, it is easier to select a hollow fiber made of an inexpensive material as the hollow fiber 4a of the hollow fiber membrane contactor 4. In addition, even if the absorbing liquid 1 in which increase in the temperature thereof reduces absorption efficiency of the gaseous hydrogen sulfide is used, the absorbing liquid 1 can absorb the gaseous hydrogen sulfide 31 before the sulfide ion 32 reacts with the oxidizer 2 to increase the temperature of the absorbing liquid 1; therefore, reduction in absorption efficiency of the gaseous hydrogen sulfide 31 by the absorbing liquid 1 attributed to increase in the temperature thereof can be suppressed.

Several inlet side flow cells 4R and outlet side flow cells 4S (see FIGS. 3, 4A and 4B), which were made of polytetrafluoroethylene (PTFE) and polyethylene and processed into various sizes and content volumes, were evaluated from the viewpoint of response sensitivity. In all the cases, in order to minimize heat capacity, the total weight of the flow cell was kept as small as possible, and the wall thickness thereof was produced as thin (approximately 1 mm) as possible. Thereby, the temperature change to be measured is larger, so that measurement sensitivity is higher.

Figure 5:
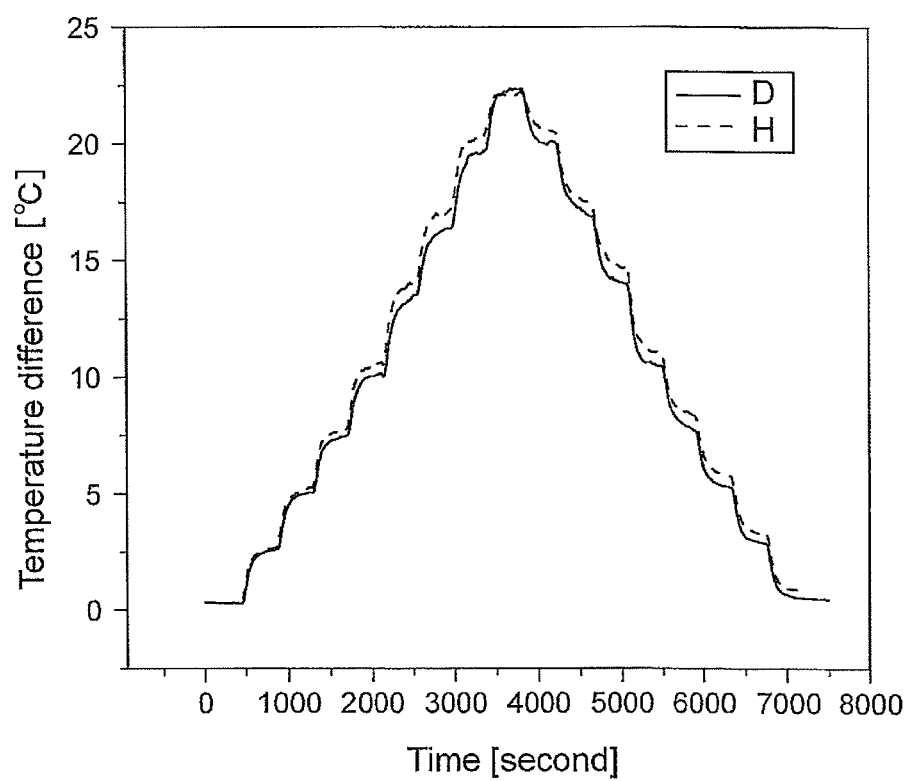
FIG. 5 is a diagram showing comparison of temperature response of the concentration measuring apparatus for hydrogen sulfide to $H_2S$ in the case where a flow cell made of PTFE (polytetrafluoroethylene) is used and in the case where a flow cell made of PE (polyethylene) is used for an inlet side flow cell and an outlet side flow cell.

FIG. 5 is a diagram showing comparison of temperature response of the concentration measuring apparatus for hydrogen sulfide to $H_2S$ in the case where a flow cell made of PTFE (polytetrafluoroethylene) is used for the inlet side flow cell and the outlet side flow cell and in the case where a flow cell made of PE (polyethylene) is used for an inlet side flow cell and an outlet side flow cell. In FIG. 5, a solid line D shows temperature response in the case where the flow cell made of PTFE is used for the inlet side flow cell and the outlet side flow cell, and a dashed line H shows temperature response in the case where the flow cell made of PE is used for the inlet side flow cell and the outlet side flow cell. As the hollow fiber membrane contactor 4, a polypropylene compact membrane module made by Membrana was used. The base line corresponds to the case where the gas flow 7 is pure nitrogen ($N_2$), and gradual change of the temperature difference corresponds to the change in the case where the $H_2S$ concentration in the gas flow 7 is increased or decreased by 6,250 ppm. NaOH at a concentration of 0.3 mol/L was used as the absorbing liquid 1, and the flow rate of the absorbing liquid 1 was 3.5 mL/min. $H_2O_2$ at a concentration of 2 mol/L was used as the oxidizer 2, and the flow rate of the oxidizer 2 was 4 mL/min.

An appropriate content volume of the flow cell cannot be determined if separated from the flow rates of both of the reagents to be used (namely, the absorbing liquid 1 and the oxidizer 2). Anyway, the optimal content volume of the flow cell is desirably a mean value between a sufficient stagnation (mixing) time in which the maximum increase in the temperature is produced in the exothermic reaction of the oxidizer 2 with the absorbed sulfide ion and the minimum stagnation time in which the response and recovery time of the measuring apparatus are shortened.

On the other hand, the influence of the flow rates of both of the reagents is described rationally as follows. Namely, when the flow rate of the absorbing liquid 1 is small, the residence time in the hollow fiber membrane contactor 4 is longer, and the absorbing liquid 1 absorbs a larger amount of hydrogen sulfide in the gas flow 7 as the sulfide ion and preconcentrates the sulfide ion, therefore resulting in higher sensitivity of the measuring apparatus results. At a certain flow rate or less (for example, in the case where a polypropylene compact module G543 made by Membrana was used), the concentration of the absorbed sulfide ion was increased, resulting in incomplete oxidation by mixing with hydrogen peroxide which is the oxidizer 2; accordingly, precipitation of sulfur was observed in the absorbing liquid 1 in the region 4BN in the vicinity of the liquid discharging end 4B. This causes adhesion of precipitating sulfur in the second thermometer 6. Consequently, in a desirable predetermined linear range, formation of sulfur sets the lower limit of the flow rate of NaOH, which is the absorbing liquid 1.

In order to make the desirable linear range wider, it is desirable that the flow rate of the absorbing liquid 1 be increased and the gas flow rate of the gas flow 7 be reduced in order to avoid formation of sulfur at a high concentration of $H_2S$. In all the cases, if the linear operating range is made wider, as it often happens, the attempt is accompanied by reduction in sensitivity. As a result of some trials, it was shown that the flow rate of hydrogen peroxide that is the oxidizer 2 is not so important as the flow rate of the absorbing liquid 1. It was further found out that a hydrogen peroxide solution in a concentration of 2 mol/L is optimal. A hydrogen peroxide solution with a higher concentration formed remarkable bubbles, resulting in production of noise in response of the measuring apparatus. On the other hand, a more diluted hydrogen peroxide solution resulted in production of sulfur at a high concentration of $H_2S$, and sensitivity and linear responsiveness were deteriorated.

Figure 6:
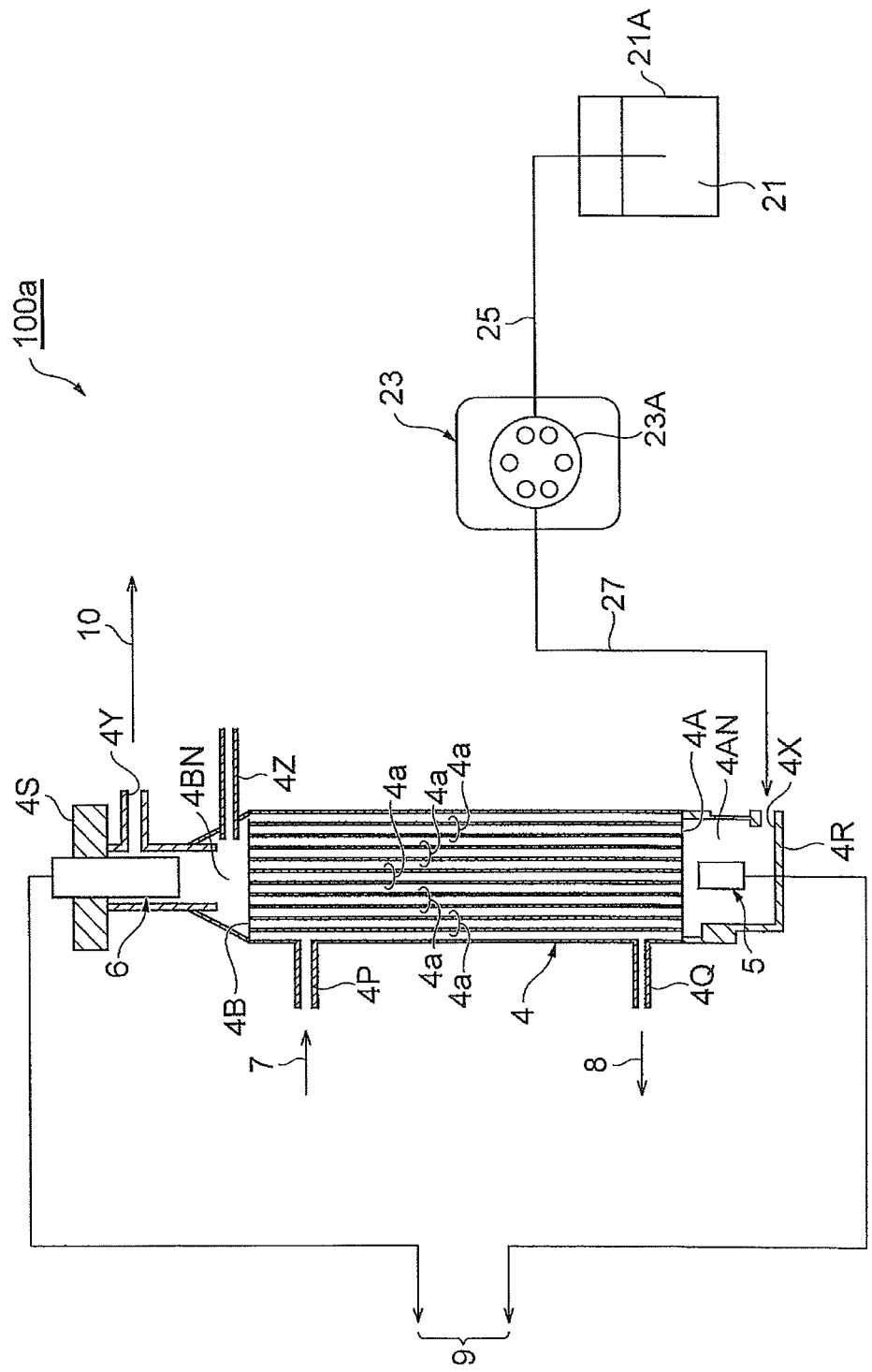
FIG. 6 is a schematic view showing a configuration of a concentration measuring apparatus for hydrogen sulfide according to a modification of the embodiment.

FIG. 6 is a schematic view showing a configuration of a concentration measuring apparatus for hydrogen sulfide according to a modification of the present embodiment. As shown in FIG. 6, the concentration measuring apparatus for hydrogen sulfide 100a according to the modification is different from the above-mentioned concentration measuring apparatus for hydrogen sulfide 100 mainly in that the concentration measuring apparatus for hydrogen sulfide 100a according to the modification includes a third container 21A instead of the first container 1A and the second container 2A, that the absorbing liquid 1 and the oxidizer 2 are mixed to be a liquid mixture 21, that the liquid mixture 21 is stored in the third container 21A, and that the concentration measuring apparatus for hydrogen sulfide 100a according to the modification includes a pump unit 23 of one channel instead of the pump unit 3 of two channels.

The pump unit 23 according to the modification of the present embodiment has a pump 23A. The pump 23A is connected with the third container 21A by a piping 25, and connected with an introducing opening 4X of the hollow fiber membrane contactor 4 by a piping 27. The pump 23A functions as the absorbing liquid feeder and the oxidizer feeder. Specifically, the pump 23A feeds the liquid mixture 21 to a region 4AN in the vicinity of the liquid introducing end 4A through the piping 25, the piping 27, and the introducing opening 4X, thereby to continuously feed the liquid mixture 21 from the liquid introducing end 4A to the tube side of the hollow fiber membrane contactor 4. In this case, the exothermic reaction of the oxidizer 2 in the liquid mixture 21 with the sulfide ion in the gas flow 7 that the absorbing liquid 1 has absorbed is made not only in a region 4BN in the vicinity of the liquid discharging end 4B but also on the tube side of the hollow fiber membrane contactor 4.

As the pump 23A, the same pump as the pump 3A for the first channel and the pump 3B for the second channel according to the first embodiment can be used.

According to the concentration measuring apparatus for hydrogen sulfide 100a according to the modification of the present embodiment as mentioned above, because the storage container of the absorbing liquid 1 and the storage container of the oxidizer 2 can be shared as the third container 21A and the feeder of the absorbing liquid 1 and the feeder of the oxidizer 2 can be shared as the pump 23A, the structure of the concentration measuring apparatus for hydrogen sulfide 100a is simplified and a more inexpensive concentration measuring apparatus for hydrogen sulfide 100a can be provided.

According to the concentration measuring apparatus for hydrogen sulfide 100 (or concentration measuring apparatus for hydrogen sulfide 100a) according to the present embodiment as mentioned above, intensity of the exothermic reaction between the sulfide ion 32 derived from the gaseous hydrogen sulfide 31 in the gas flow 7 to be measured that the absorbing liquid 1 has absorbed with the oxidizer 2 can be measured by the first thermometer 5 and the second thermometer 6. Absorption of the gaseous hydrogen sulfide 31 in the gas flow 7 by the absorbing liquid 1 (namely, movement of the gaseous hydrogen sulfide 31 from the gas flow 7 to the absorbing liquid 1 and the absorption reaction of the gaseous hydrogen sulfide 31 by the absorbing liquid 1) occurs immediately when the absorbing liquid 1 and the gas flow 7 contact each other through the hollow fiber 4a, which is the membrane of the hollow fiber membrane contactor 4, and in addition, the exothermic reaction of the sulfide ion 32 with the oxidizer 2 is made immediately when these are mixed. Thus, the concentration measuring apparatus for hydrogen sulfide 100 (or concentration measuring apparatus for hydrogen sulfide 100a) according to the present embodiment utilizes a mass transfer phenomenon at fast traveling speed and a reaction at a fast reaction rate; therefore, the concentration of the gaseous hydrogen sulfide 31 in the gas flow 7 can be continuously measured, and the concentration of the gaseous hydrogen sulfide 31 in the gas flow 7 can also be measured in real time.

In the absorption reaction of the gaseous hydrogen sulfide 31 by the absorbing liquid 1 and the exothermic reaction of the sulfide ion 32 and the oxidizer 2, a catalyst is unnecessary. Moreover, because $H_2S$ of the gas flow 7 is selectively absorbed by the absorbing liquid 1 using the hollow fiber 4a of the hollow fiber membrane contactor 4 even if moisture is contained in the gas flow 7, almost no influence is given to a measured value of the moisture in the gas flow 7. Moreover, in the concentration measuring apparatus for hydrogen sulfide 100 (or the concentration measuring apparatus for hydrogen sulfide 100a) according to the present embodiment, a component that limits the life span of the apparatus as that in the conventional measuring apparatus is unnecessary. For these reasons, reliability of the concentration measuring apparatus for hydrogen sulfide 100 according to the present embodiment (or the concentration measuring apparatus for hydrogen sulfide 100a) is enhanced. Further, to exothermically react the sulfide ion 32 with the oxidizer 2 and to measure intensity of this exothermic reaction, a complicated component and an expensive component are unnecessary. For that reason, in the concentration measuring apparatus for hydrogen sulfide 100 (or the concentration measuring apparatus for hydrogen sulfide 100a), the configuration thereof is simple and the price thereof is inexpensive.

According to the concentration measuring apparatus for hydrogen sulfide 100 (or the concentration measuring apparatus for hydrogen sulfide 100a) according to the present embodiment, because the concentration of the gaseous hydrogen sulfide 31 is in direct proportion to the temperature difference $\Delta T$ (temperature difference $\Delta T$ between the temperature of the absorbing liquid 1 before the exothermic reaction step and the temperature of the absorbing liquid 1 after the exothermic reaction step) in a wide range of the concentration of the gaseous hydrogen sulfide in the gas flow 7, a wide operating range of the linear relationship from the ppm level to the percent level can be obtained in measurement of the concentration of the gaseous hydrogen sulfide 31 in the gas flow 7.

According to the method for determining sulfide ion according to the present embodiment as mentioned above, intensity of the exothermic reaction of the sulfide ion 32 in the absorption liquid 1 to be determined with the oxidizer 2 can be calculated from a difference between the temperature of the liquid before the exothermic reaction is made and that after the exothermic reaction is made. The exothermic reaction of the sulfide ion 32 with the oxidizer 2 is made immediately when these are mixed. Thus, because the determination method according to the present embodiment utilizes a reaction at a fast reaction rate, the determination method can continuously determine the sulfide ion 32 in the flow of the absorbing liquid 1 even if the absorbing liquid 1 flows, and can also measure the concentration of the sulfide ion 32 in the absorbing liquid 1 in real time.

Further, in the exothermic reaction of the sulfide ion 32 with an oxidizer 2, a catalyst is unnecessary. For that reason, reliability of determination is enhanced. Further, to exothermically react the sulfide ion with the oxidizer 2 and to measure intensity of this exothermic reaction, a complicated component and an expensive component are unnecessary. Thereby, the determination method according to the present embodiment can be implemented as an inexpensive apparatus with a simple configuration. For that reason, the determination method according to the present embodiment can be used for the concentration measuring apparatus for hydrogen sulfides 100 (or concentration measuring apparatus for hydrogen sulfide 100a) as mentioned above.

Moreover, according to the method for determining sulfide ion according to the present embodiment as mentioned above, because the concentration of the sulfide ion 32 is in direct proportion to the temperature difference $\Delta T$ (temperature difference $\Delta T$ between the temperature of the absorbing liquid 1 before the exothermic reaction step and the temperature of the absorbing liquid 1 after the exothermic reaction step) in a wide range of the concentration of the sulfide ion 32 in the absorbing liquid 1, determination of the concentration of the sulfide ion 32 can be easily performed from the ppm level to the percent level in measurement of the concentration of the sulfide ion 32 in the absorbing liquid 1.

Hereinafter, in order to make the effect of the present invention clearer, the present invention will be described using Examples. In the experiment of each following Example, in order to obtain a mixed gas containing a predetermined gas (for example, $H_2S$) at a predetermined concentration, a gas mixer of four channels having four mass flow rate controllers was used. For example, in order to obtain a mixed gas of $H_2S$ and gaseous nitrogen, a gas mixer formed of one mass flow rate controller for nitrogen and three mass flow rate controllers for $H_2S$ whose controllable ranges were different was used. By these mass flow rate controllers, the gas flow consisting of the mixed gas of nitrogen and $H_2S$ mixed at a predetermined proportion was prepared exactly, and the mixed gas of $H_2S$ and gaseous nitrogen was fed to the shell side of the hollow fiber membrane contactor 4. By using three mass flow rate controllers for $H_2S$ whose controllable ranges were different, several kinds of gas flows of several kinds of the mixed gas in which the concentration of $H_2S$ was changed in a wide range (range from the ppm level to the percent level) were prepared.

Example 1

Figure 7:
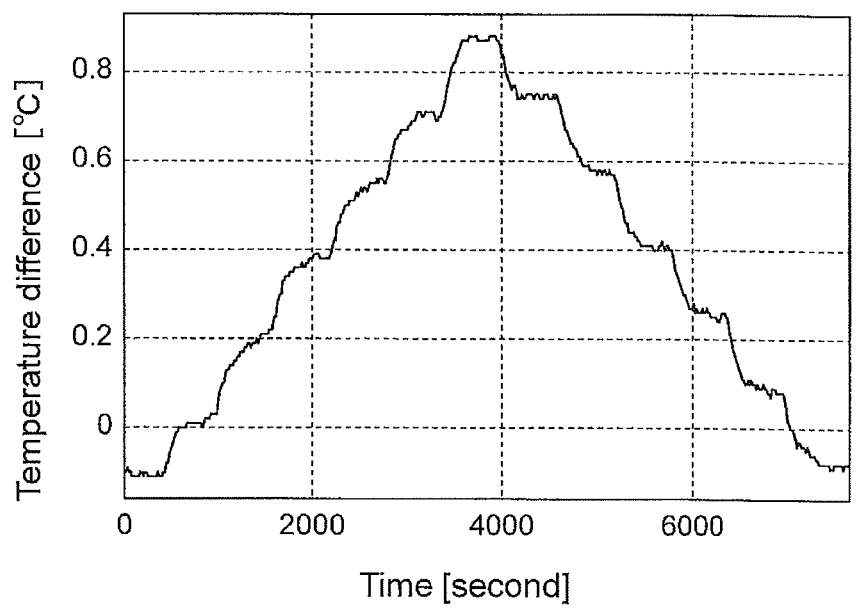
FIG. 7 is a diagram showing temperature response to gradual change of an $H_2S$ concentration in a gas flow in a low concentration region.

FIG. 7 is a diagram showing temperature response to series of step changes of $H_2S$ concentration in a gas flow in a low concentration region. As the hollow fiber membrane contactor 4, a polypropylene compact membrane module made by Membrana was used. Gradual change of temperature difference corresponds to change in the case where the $H_2S$ concentration in the gas flow 7 was increased or decreased by 250 ppm (0.025%). NaOH at a concentration of 0.3 mol/L was used as the absorbing liquid 1, and the flow rate of the absorbing liquid 1 was 2 mL/min. $H_2O_2$ at a concentration of 2 mol/L was used as the oxidizer 2, and the flow rate of the oxidizer 2 was 2 mL/min. FIG. 7 shows the result obtained about the temperature response of the measuring apparatus in a lower concentration range of $H_2S$ compared with the result shown in FIG. 5.

Example 2

Figure 8:
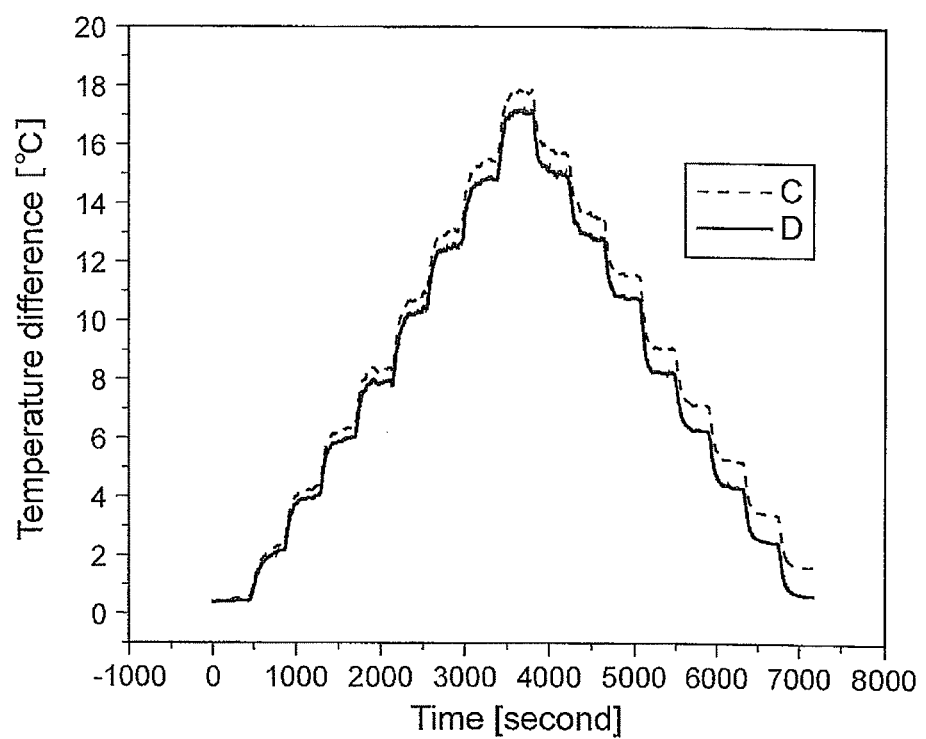
FIG. 8 is a diagram showing an example in which superiority of temperature difference measurement in the present invention is proved.

FIG. 8 is a diagram showing an example in which superiority of temperature difference measurement in the present invention is proved. A solid line D shows the result based on temperature difference measurement according to the present invention (measurement of the difference between the measured value by the second thermometer 6 and that by the first thermometer 5), and a dashed line C shows the result based on the difference between the measured value by the second thermometer 6 and an initial input temperature (the first measured value by the first thermometer 5) as Comparative Example. Use of the difference between the measured value by the second thermometer 6 and the initial input temperature in the case of Comparative Example is for giving the zero base line in Comparative Example so that the temperature difference measurement can be easily compared with the measurement only by the second thermometer 6. (At first, the measured value of the first thermometer 5=the measured value of the second thermometer 6, and the difference between the measured value by the second thermometer 6 and that by the first thermometer 5 is zero.)

In the measurement shown in FIG. 8, a cell made of PTFE (7 g) was used. Gradual change of the temperature corresponds to change in the case where the $H_2S$ concentration in the gas flow 7 was increased or decreased by 6,250 ppm. NaOH at a concentration of 0.3 mol/L was used as the absorbing liquid 1, and the flow rate of the absorbing liquid 1 was 4 mL/min. $H_2O_2$ at a concentration of 1 mol/L was used as the oxidizer 2, and the flow rate of the oxidizer 2 was 4 mL/min.

As shown in FIG. 8, the temperature of the absorbing liquid 1 in the region 4AN in the vicinity of the liquid introducing end 4A changed with time, and influenced reproducibility of the signal only based on the measured value of the second thermometer 6. On the other hand, in the signal in which the analysis signal was based on the temperature difference (namely, the measured value of the second thermometer 6—the measured value of the first thermometer 5), most of this inconvenient influence accompanying the temperature change of the absorbing liquid 1 was eliminated.

Example 3

FIGS. 9A, 9B, 9C, 9D and 9E are diagrams showing reproducibility of response of the measuring apparatus to gradual change between zero gas and various $H_2S$ concentrations in a gas flow. A polypropylene membrane module was used as the hollow fiber membrane contactor 4. Moreover, in FIG. 9A, step change of the temperature difference corresponds to change in the case where the $H_2S$ concentration in the gas flow 7 was increased or decreased step by step between 0 ppm and 25,000 ppm. NaOH at a concentration of 0.3 mol/L was used as the absorbing liquid 1, and the flow rate of the absorbing liquid 1 was 4 mL/min. $H_2O_2$ at a concentration of 2 mol/L was used as the oxidizer 2, and the flow rate of the oxidizer 2 was 4 mL/min. The flow rate of the gas flow 7 was 200 mL/min.

Figure 9C:
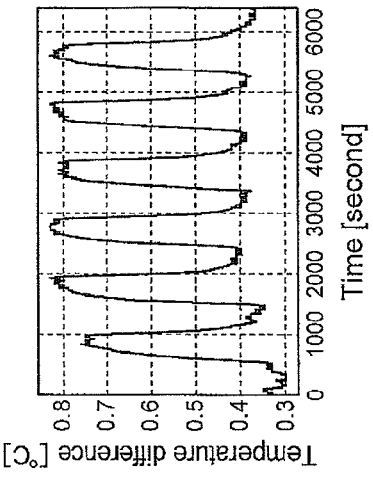
FIG. 9C is a diagram showing reproducibility of response of the measuring apparatus to step 1 change between zero gas and various $H_2S$ concentrations in a gas flow.
Figure 9B:
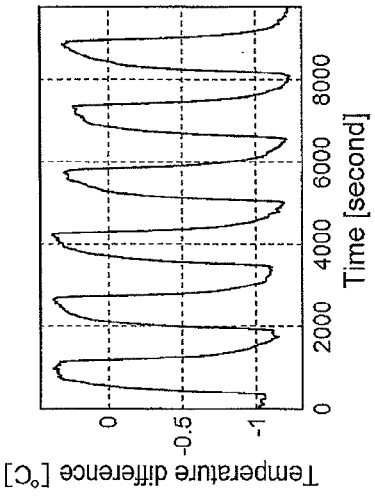
FIG. 9B is a diagram showing reproducibility of response of the measuring apparatus to step change between zero gas and various $H_2S$ concentrations in a gas flow.
Figure 9A:
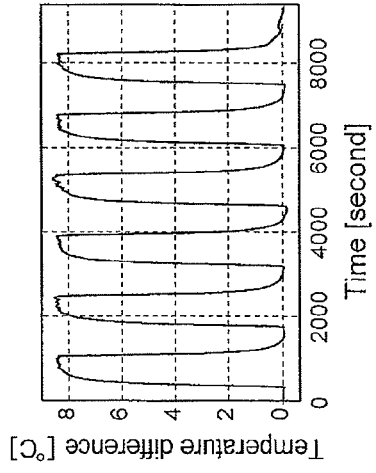
FIG. 9A is a diagram showing reproducibility of response of the measuring apparatus to step change between zero gas and various $H_2S$ concentrations in a gas flow.

In FIG. 9B, gradual change of the temperature difference corresponds to change in the case where the $H_2S$ concentration in the gas flow 7 was increased or decreased step by step between 0 ppm and 1,250 ppm. NaOH at a concentration of 0.3 mol/L was used as the absorbing liquid 1, and the flow rate of the absorbing liquid 1 was 4 mL/min. $H_2O_2$ at a concentration of 2 mol/L was used as the oxidizer 2, and the flow rate of the oxidizer 2 was 4 mL/min. The flow rate of the gas flow 7 was 200 mL/min.

In FIG. 9C, gradual change of the temperature difference corresponds to change in the case where the $H_2S$ concentration in the gas flow 7 was increased or decreased step by step between 0 ppm and 833 ppm. NaOH at a concentration of 0.3 mol/L was used as the absorbing liquid 1, and the flow rate of the absorbing liquid 1 was 4 mL/min. $H_2O_2$ at a concentration of 2 mol/L was used as the oxidizer 2, and the flow rate of the oxidizer 2 was 4 mL/min. The flow rate of the gas flow 7 was 600 mL/min.

Figure 9E:
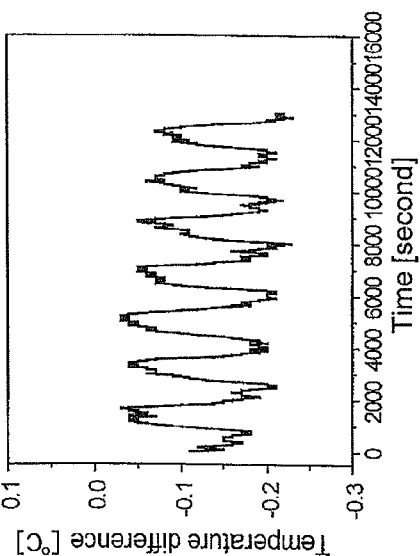
FIG. 9E is a diagram showing reproducibility of response of the measuring apparatus to step 1 change between zero gas and various $H_2S$ concentrations in a gas flow.
Figure 9D:
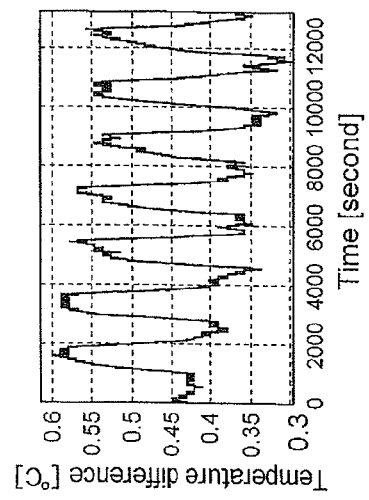
FIG. 9D is a diagram showing reproducibility of response of the measuring apparatus to step change between zero gas and various $H_2S$ concentrations in a gas flow.

In FIG. 9D, gradual change of the temperature difference corresponds to change in the case where the $H_2S$ concentration in the gas flow 7 was increased or decreased step by step between 0 ppm and 250 ppm. NaOH at a concentration of 0.3 mol/L was used as the absorbing liquid 1, and the flow rate of the absorbing liquid 1 was 1.3 mL/min. $H_2O_2$ at a concentration of 2 mol/L was used as the oxidizer 2, and the flow rate of the oxidizer 2 was 1.3 mL/min. The flow rate of the gas flow 7 was 200 mL/min.

In FIG. 9E, gradual change of the temperature difference corresponds to change in the case where the $H_2S$ concentration in the gas flow 7 was increased or decreased step by step between 0 ppm and 125 ppm. NaOH at a concentration of 0.3 mol/L was used as the absorbing liquid 1, and the flow rate of the absorbing liquid 1 was 1.25 mL/min. $H_2O_2$ at a concentration of 2 mol/L was used as the oxidizer 2, and the flow rate of the oxidizer 2 was 1.25 mL/min. The flow rate of the gas flow 7 was 400 mL/min.

The reproducibility of response of the measuring apparatus was evaluated at different $H_2S$ concentration levels, and the obtained results were shown in FIGS. 9A, 9B, 9C, 9D and 9E. Under predetermined experimental conditions, the $H_2S$ concentration in the gas flow 7 was changed step by step several times between zero (pure $N_2$) and a predetermined concentration. That peaks of the signal are close was considered as a scale of the reproducibility of the signal.

Example 4

Figure 10:
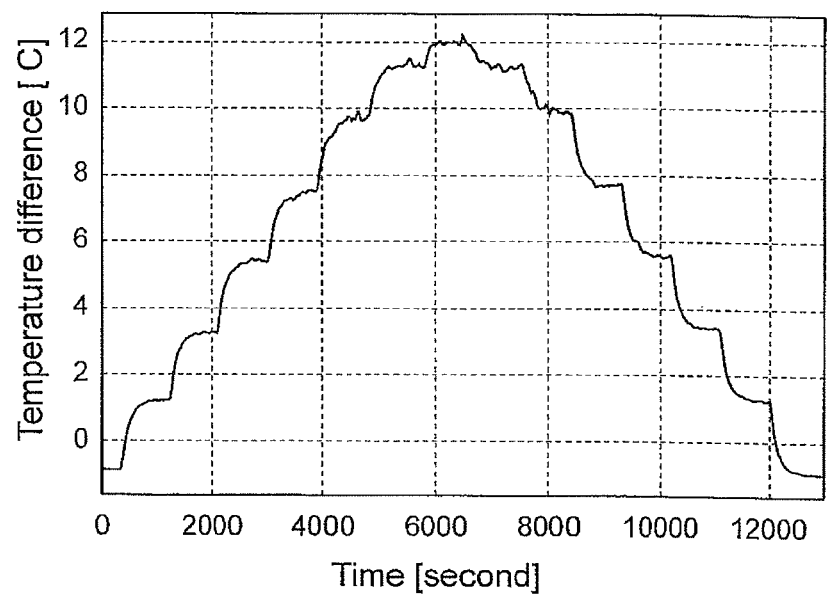
FIG. 10 is a diagram showing the calorimetric response under conditions suitable for increasing sensitivity.

FIG. 10 is a diagram showing responsiveness of thermometry on conditions suitable for increasing sensitivity. A polypropylene membrane module was used as the hollow fiber membrane contactor 4. In FIG. 10, gradual change of temperature difference corresponds to change in the case where the $H_2S$ concentration in the gas flow 7 was increased or decreased by 1,250 ppm. NaOH at a concentration of 0.3 mol/L was used as the absorbing liquid 1, and the flow rate of the absorbing liquid 1 was 2 mL/min. $H_2O_2$ at a concentration of 2 mol/L was used as the oxidizer 2, and the flow rate of the oxidizer 2 was 2 mL/min. The flow rate of the gas flow 7 was 600 mL/min.

A calibration curve obtained on conditions on which high sensitivity is obtained at the sacrifice of a wide linear range is shown in FIG. 10. A case where the gas flow rate of the gas flow 7 was large and the liquid flow rate of the absorbing liquid 1 was relatively small was included in such conditions. A limit at which linearity was obtained (namely, 8,000 ppm) is determined by precipitation formation of sulfur. This is remarkably lower than the limit of linearity of 50,000 ppm obtained at a flow rate of the gas flow 7 of 200 mL/min, a flow rate of $H_2O_2$ of 4 mL/min as the oxidizer 2, and a flow rate of NaOH of 4 mL/min as the absorbing liquid 1 (the limit of linearity obtained in Example 2 corresponding to FIG. 8).

Example 5

Figure 11:
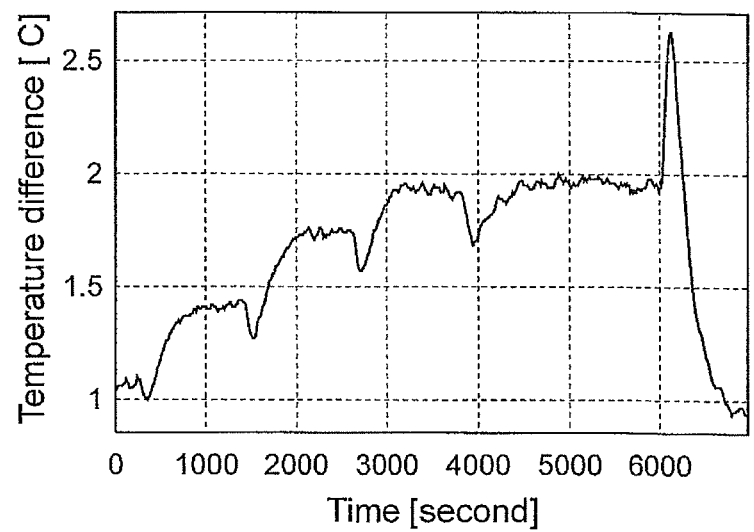
FIG. 11 is a diagram showing responsiveness of thermometry to $CO_2$ in the gas flow when $H_2S$ does not exist.

FIG. 11 is a diagram showing responsiveness of thermometry of a mixed gas of $N_2$ and $CO_2$ when $H_2S$ does not exist. In FIG. 11, gradual increases in the $CO_2$ concentration in $N_2$ respectively correspond to 0%, 2.5%, 5%, 7.5%, and 10%. NaOH at a concentration of 0.3 mol/L was used as the absorbing liquid 1, and the flow rate of the absorbing liquid 1 was 2 mL/min. $H_2O_2$ at a concentration of 2 mol/L was used as the oxidizer 2, and the flow rate of the oxidizer 2 was 2 mL/min. The flow rate of the gas flow 7 was 200 mL/min.

The response selectivity of thermometry to $H_2S$ was evaluated in the presence of $CO_2$ that usually coexists with $H_2S$ in the natural gas. It is thought that $CO_2$ gives weak interference because of the dissolution and absorption reaction with the NaOH absorbing liquid, which is the absorbing liquid 1. FIG. 11 shows response to increase in the $CO_2$ concentration in the gas flow 7 consisting of the mixed gas of $N_2$ and $CO_2$ in which $H_2S$ does not exist. The obtained result showed response sufficiently smaller than the result obtained in the case where the gas flow 7 contains only $H_2S$ in $N_2$ (approximately 1.4% of the case where the gas flow 7 contains only $H_2S$ in $N_2$). $H_2S$ acts as both of a weak acid and a reducing agent, and mainly causes the heating effect. This conclusion is further verified by data shown in FIG. 12.

Figure 12:
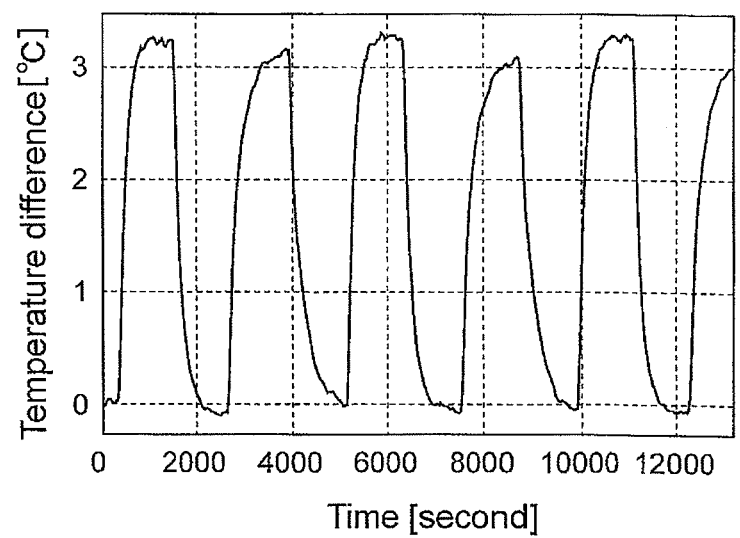
FIG. 12 is a diagram showing a series of step change that shows selectivity of the $H_2S$ concentration measuring apparatus when $CO_2$ exists.

FIG. 12 is a diagram showing a series of gradual change that shows selectivity of the concentration measuring apparatus for hydrogen sulfide when $CO_2$ exists. NaOH at a concentration of 0.3 mol/L was used as the absorbing liquid 1, and the flow rate of the absorbing liquid 1 was 2 mL/min. $H_2O_2$ at a concentration of 2 mol/L was used as the oxidizer 2, and the flow rate of the oxidizer 2 was 2 mL/min. In FIG. 12, the gas flow 7 consists of 20 mL of $H_2S$ at a concentration of 5% and 180 mL of $N_2$ in the first, third, and fifth phases (namely, the gas flow 7 contains $H_2S$ at a concentration of 0.5%). The gas flow 7 consists of 18 mL of $H_2S$ at a concentration of 5%, 2 mL of $CO_2$ at a concentration of 100%, and 180 mL of $N_2$ in the second, fourth, and sixth phases (namely, the gas flow 7 contains $H_2S$ at a concentration of 0.45% and $CO_2$ at a concentration of 1%).

In FIG. 12, compared with the first, third, and fifth phases from the left side thereof, 2 mL of $H_2S$ at a concentration of 5% was replaced by 2 mL of $CO_2$ at a concentration of 100% (namely, 20 times as much as $H_2S$) in the second, fourth, and sixth phases. FIG. 12 shows that the response of $CO_2$ is apparently smaller than that of $H_2S$ even if part of $H_2S$ is replaced by $CO_2$ 20 times as much as $H_2S$ and the signal is reduced.

Figure 13A:
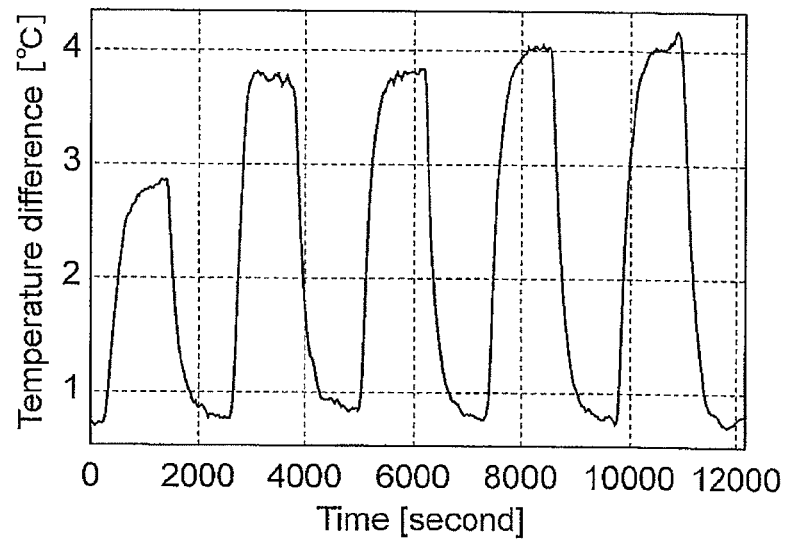
FIG. 13A is a diagram showing selectivity of the calorimetric response to $H_2S$.
Figure 13B:
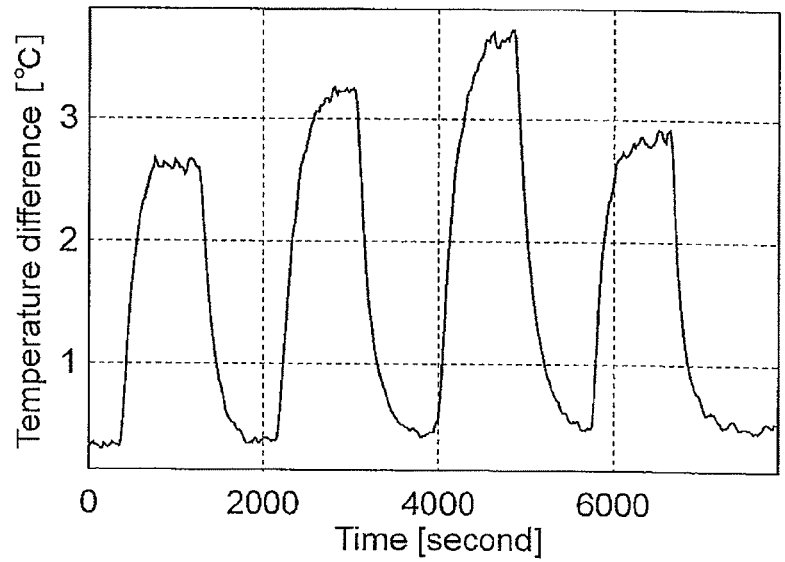
FIG. 13B is a diagram showing selectivity of the calorimetric response to $H_2S$.

FIGS. 13A and 13B are diagrams showing selectivity of the calorimetric response to $H_2S$. In FIG. 13A, NaOH at a concentration of 0.5 mol/L was used as the absorbing liquid 1, and the flow rate of the absorbing liquid 1 was 2 mL/min. $H_2O_2$ at a concentration of 2 mol/L was used as the oxidizer 2, and the flow rate of the oxidizer 2 was 2 mL/min. The flow rate of the gas flow 7 was 200 mL/min. In all the phases, the gas flow 7 contained 0.5% of $H_2S$. The amount of $CO_2$ was 0 mL in the first phase from the left side, 5 mL in the second phase from the left side, 10 mL in the third phase from the left side, 15 mL in the fourth phase from the left side, and 20 mL in the fifth phase from the left side. In the first phase to the fifth phase, the $CO_2$ concentrations in the gas flow 7 respectively correspond to 0%, 2.5%, 5%, 7.5%, and 10%.

In FIG. 13B, NaOH at a concentration of 0.5 mol/L was used as the absorbing liquid 1, and the flow rate of the absorbing liquid 1 was 2 mL/min. $H_2O_2$ at a concentration of 2 mol/L was used as the oxidizer 2, and the flow rate of the oxidizer 2 was 2 mL/min. The flow rate of the gas flow 7 was 200 mL/min. In all the phases, the gas flow 7 contained 0.5% of $H_2S$. While the $H_2S$ concentration and the $CO_2$ concentration in the gas flow 7 in the first phase and the second phase from the left side are the same as the case shown in FIG. 13A (namely, the H₂S concentration in the gas flow 7 is 0.5% in both of the phases and the CO₂ concentrations are respectively 0% and 2.5%), the H₂S concentration is equivalent to 0.5% and the CO₂ concentration is equivalent to 7.5% in the third phase, and H₂S is equivalent to 0.5% and the CO₂ concentration is equivalent to 0% in the fourth phase (namely, the same conditions as those in the first phase). In the fourth phase, a small influence produced subsequently was verified by exposure to 7.5% of CO₂ in the third phase, which was for verifying reproducibility of the first phase.

The results shown in FIGS. 13A and 13B verified the conclusion obtained from FIG. 12. Namely, comparing the first phase of FIG. 13A with the fifth phase thereof, 10% of CO₂ produced a small signal (approximately 1° C.), and the signal was not increased linearly even if the CO₂ concentration was increased from the first phase to the fifth phase.

What is claimed is:

1. A measuring apparatus that measures a concentration of gaseous hydrogen sulfide in a gas flow, the measuring apparatus comprising:

an absorbing liquid that can absorb gaseous hydrogen sulfide as sulfide ion, the absorbing liquid being an alkaline solution;

a hollow fiber membrane module comprising a plurality of hollow fiber membranes, an inlet and an outlet for the gas flow provided on the shell side of the hollow fiber membrane module, and a liquid introducing end and a liquid discharging end for the absorbing liquid provided on the tube side of the hollow fiber membrane module, the hollow fiber membrane module contacting the gas flow with a flow of the absorbing liquid through membranes of the plurality of hollow fiber membranes, so that the absorbing liquid absorbs at least part of gaseous hydrogen sulfide in the gas flow as sulfide ion;

an absorbing liquid feeder that feeds the absorbing liquid to the liquid introducing end of the hollow fiber membrane module;

an oxidizer that exothermically reacts with sulfide ion;

an oxidizer feeder that feeds the oxidizer to the absorbing liquid;

a first thermometer that measures a temperature of the absorbing liquid before the sulfide ion that the absorbing liquid has absorbed exothermically reacts with the oxidizer;

a second thermometer that measures the temperature of the absorbing liquid after the sulfide ion that the absorbing liquid has absorbed exothermically reacts with the oxidizer; and an alkali trap connected to the outlet for the gas flow, wherein the oxidizer feeder feeds the oxidizer to the absorbing liquid after the absorbing liquid absorbs the at least part of the gaseous hydrogen sulfide.

2. The measuring apparatus according to claim 1, wherein the oxidizer is hydrogen peroxide or hypochlorite.

3. The measuring apparatus according to claim 1, further comprising:

a first container that stores the absorbing liquid; and a second container that stores the oxidizer.

4. The measuring apparatus according to claim 1, wherein the oxidizer feeder feeds the oxidizer to the absorbing liquid in a region in the vicinity of a the liquid discharging end of the hollow fiber membrane module.

5. The measuring apparatus according to claim 1, further comprising a third container that stores a liquid mixture of the absorbing liquid and the oxidizer.

6. A method for measuring a concentration of gaseous hydrogen sulfide in a gas flow, the method comprising:

(a) flowing an absorbing liquid through a tube side of a hollow fiber membrane module comprising a plurality of hollow fiber membranes, the absorbing liquid being an alkaline solution, (b) flowing the gas flow through a shell side of the hollow fiber membrane module, (c) contacting the gas flow with a flow of the absorbing liquid through membranes of the plurality of hollow fiber membranes, so that the absorbing liquid absorbs at least part of gaseous hydrogen sulfide in the gas flow as sulfide ion, (d) feeding an oxidizer to the absorbing liquid after the step (c), (e) flowing the gas flow through an alkali trap connected to an outlet for the gas flow of the hollow fiber membrane module after the step (c), (f) exothermically reacting sulfide ion in the absorbing liquid with the oxidizer; and (g) calculating a determination value of the sulfide ion based on a difference between a temperature of the absorbing liquid before the exothermic reaction step and a temperature of the absorbing liquid after the exothermic reaction step.

7. The method according to claim 6, wherein the oxidizer is hydrogen peroxide or hypochlorite.

* * * * *

UNITED STATES PATENT AND TRADEMARK OFFICE
CERTIFICATE OF CORRECTION

PATENT NO.         : 8,709,820 B2
APPLICATION NO.    : 13/036535
DATED              : April 29, 2014
INVENTOR(S)        : S. Marzouk et al.

Page 1 of 1

It is certified that error appears in the above-identified patent and that said Letters Patent is hereby corrected as shown below:

Title Page 2, item (56), Column 1, line 27, References Cited, Other Publications, of the printed patent, "Tencnology" should read --Technology--.

Title Page 2, item (56), Column 1, line 32, References Cited, Other Publications, of the printed patent, "Jrournal" should read --Journal--.

Title Page 2, item (56), Column 2, line 29, References Cited, Other Publications, of the printed patent, "Suffer" should read --Sulfer-- before Energy.

Title Page 2, item (56), Column 2, line 16, References Cited, Other Publications, of the printed patent, "sul?de" should read --sulfide-- before Energy.

Title Page 2, item (56), Column 2, line 25, References Cited, Other Publications, of the printed patent, "Sul?de" should read --Sulfide-- before Energy.

In the Claims

At Column 20, line 12 (Claim 4, line 3) of the printed patent, delete "a" before the.

Signed and Sealed this
Third Day of February, 2015

Michelle K. Lee
*Deputy Director of the United States Patent and Trademark Office*